(12) United States Patent
Kishi

(10) Patent No.: US 8,371,846 B2
(45) Date of Patent: Feb. 12, 2013

(54) SELF-ADJUSTABLE, SELF-LIGATING ORTHODONTIC BRACKET

(76) Inventor: Mohannad Kishi, Dubai (AE)

( * ) Notice: Subject to any disclaimer, the term of this patent is extended or adjusted under 35 U.S.C. 154(b) by 0 days.

(21) Appl. No.: 12/939,712

(22) Filed: Nov. 4, 2010

(65) Prior Publication Data

US 2011/0300502 A1 Dec. 8, 2011

Related U.S. Application Data

(60) Provisional application No. 61/350,966, filed on Jun. 3, 2010.

(51) Int. Cl.
*A61C 7/14* (2006.01)
*A61C 7/30* (2006.01)

(52) U.S. Cl. .................. 433/16; 433/9; 433/11

(58) Field of Classification Search ............ 433/3, 6–14, 433/16, 26
See application file for complete search history.

(56) References Cited

U.S. PATENT DOCUMENTS

| | | | | |
|---|---|---|---|---|
| 4,243,387 A * | 1/1981 | Prins | ................ | 433/16 |
| 4,597,739 A | 7/1986 | Rosenberg | | |
| 4,725,229 A | 2/1988 | Miller | | |
| 5,037,297 A * | 8/1991 | Lerner | ............ | 433/14 |
| 5,269,681 A * | 12/1993 | Degnan | ........... | 433/11 |
| 5,954,502 A | 9/1999 | Tuenge et al. | | |
| 6,036,488 A * | 3/2000 | Williams | ........... | 433/19 |
| 6,217,321 B1 * | 4/2001 | Kanno | ............ | 433/11 |
| 6,866,505 B2 * | 3/2005 | Senini | ............ | 433/10 |
| 7,306,458 B1 | 12/2007 | Lu | | |
| 7,431,586 B1 * | 10/2008 | Silverman | ......... | 433/9 |
| 2006/0008761 A1 | 1/2006 | Allred | | |
| 2006/0228664 A1 | 10/2006 | Castner et al. | | |
| 2006/0269763 A1 | 11/2006 | Nakano et al. | | |
| 2006/0269895 A1 | 11/2006 | Voudouris | | |
| 2007/0015104 A1 | 1/2007 | Wiechmann et al. | | |
| 2007/0072143 A1 | 3/2007 | Sommer | | |
| 2007/0082315 A1 | 4/2007 | Sabater | | |
| 2007/0128571 A1 | 6/2007 | Kimura | | |
| 2007/0148610 A1 | 6/2007 | Lai et al. | | |
| 2007/0178422 A1 | 8/2007 | Voudouris | | |
| 2007/0224569 A1 | 9/2007 | Oda | | |
| 2007/0231767 A1 * | 10/2007 | Sears et al. | ........ | 433/8 |
| 2007/0243497 A1 | 10/2007 | Voudouris | | |
| 2007/0248928 A1 | 10/2007 | Damon | | |
| 2007/0259302 A1 | 11/2007 | Jayawardena | | |
| 2007/0264606 A1 | 11/2007 | Muha et al. | | |
| 2007/0275342 A1 | 11/2007 | Oda | | |
| 2008/0014544 A1 | 1/2008 | Nucera | | |
| 2008/0241782 A1 | 10/2008 | Abels et al. | | |
| 2008/0293005 A1 * | 11/2008 | Rahlis et al. | ............ | 433/16 |
| 2008/0311534 A1 | 12/2008 | Farzin-Nia et al. | | |
| 2009/0061376 A1 | 3/2009 | Wool | | |
| 2009/0075227 A1 | 3/2009 | Opin et al. | | |
| 2009/0111067 A1 | 4/2009 | Tsukuma et al. | | |
| 2009/0117512 A1 | 5/2009 | Minium | | |
| 2009/0155734 A1 | 6/2009 | Damon | | |

(Continued)

OTHER PUBLICATIONS

PCT/IB2011/001566, 2723.21pct, International Search Report and Written Opinion of the International Searching Authority.

*Primary Examiner* — Cris L Rodriguez
*Assistant Examiner* — Matthew Seward
(74) *Attorney, Agent, or Firm* — Kunzler Law Group, PC

(57) ABSTRACT

A self-adjustable, self-ligating orthodontic bracket includes a base with a tooth face bonded to a surface of a tooth. A linking body includes a body connection. The linking body is in physical communication with an archwire transmitting a force to the linking body. A connector applies a tension between the linking body and the base motivating the linking body and the base toward a normal position.

20 Claims, 26 Drawing Sheets

U.S. PATENT DOCUMENTS

| | | |
|---|---|---|
| 2009/0162807 A1 | 6/2009 | Hagelganz et al. |
| 2009/0170049 A1 | 7/2009 | Heiser |
| 2009/0220907 A1 | 9/2009 | Suyama |
| 2009/0286195 A1 | 11/2009 | Sears et al. |
| 2009/0291404 A1 | 11/2009 | Oda |
| 2009/0298003 A1 | 12/2009 | Wei et al. |
| 2009/0325118 A1 | 12/2009 | Lewis et al. |
| 2009/0325120 A1 | 12/2009 | Lewis et al. |
| 2010/0000069 A1 | 1/2010 | Voudouris |
| 2010/0055637 A1 | 3/2010 | Rodriguez et al. |
| 2010/0062387 A1 | 3/2010 | Hilliard |
| 2010/0105000 A1 | 4/2010 | Scommegna et al. |
| 2010/0129764 A1 | 5/2010 | Pospisil |

\* cited by examiner

SELF-ADJUSTABLE, SELF-LIGATING ORTHODONTIC BRACKET

CROSS-REFERENCE TO RELATED APPLICATIONS

This application claims priority to U.S. Provisional Patent Application No. 61/350,966 entitled "SELF-ADJUSTABLE SELF-LIGATING ORTHODONTIC BRACKET" and filed on Jun. 3, 2010 for Mohannad Kishi, which is incorporated herein by reference.

FIELD

The subject matter disclosed herein relates to orthodontic brackets and more particularly relates to self-adjustable, self-ligating orthodontic brackets.

BACKGROUND

An orthodontist corrects a position of a tooth by bonding a bracket to the tooth. The bracket is then litigated to an archwire. The archwire transfers of force to the bracket, motivating the tooth to a new position within the mouth.

Unfortunately, the archwire and the connection of the bracket to the archwire must be regularly modified as the position of the tooth shifts within the mouth so that the force from the archwire continues to motivate the tooth in the desired direction. The cost of orthodontic treatment is increased as this modification of the archwire and the connection to the bracket is needed more frequently.

In addition, the orthodontist must often ligate the bracket to the archwire using bands or wires. The time required to litigate the bracket to the archwire further increases the cost of orthodontic treatment.

BRIEF DESCRIPTION OF THE DRAWINGS

A more particular description of the embodiments briefly described herein will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Based on the foregoing discussion, the inventor has recognized a need for a self-adjustable, self-ligating apparatus and method. Beneficially, such as apparatus and method would provide more efficient and cost-effective orthodontic treatment.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Figure 1:
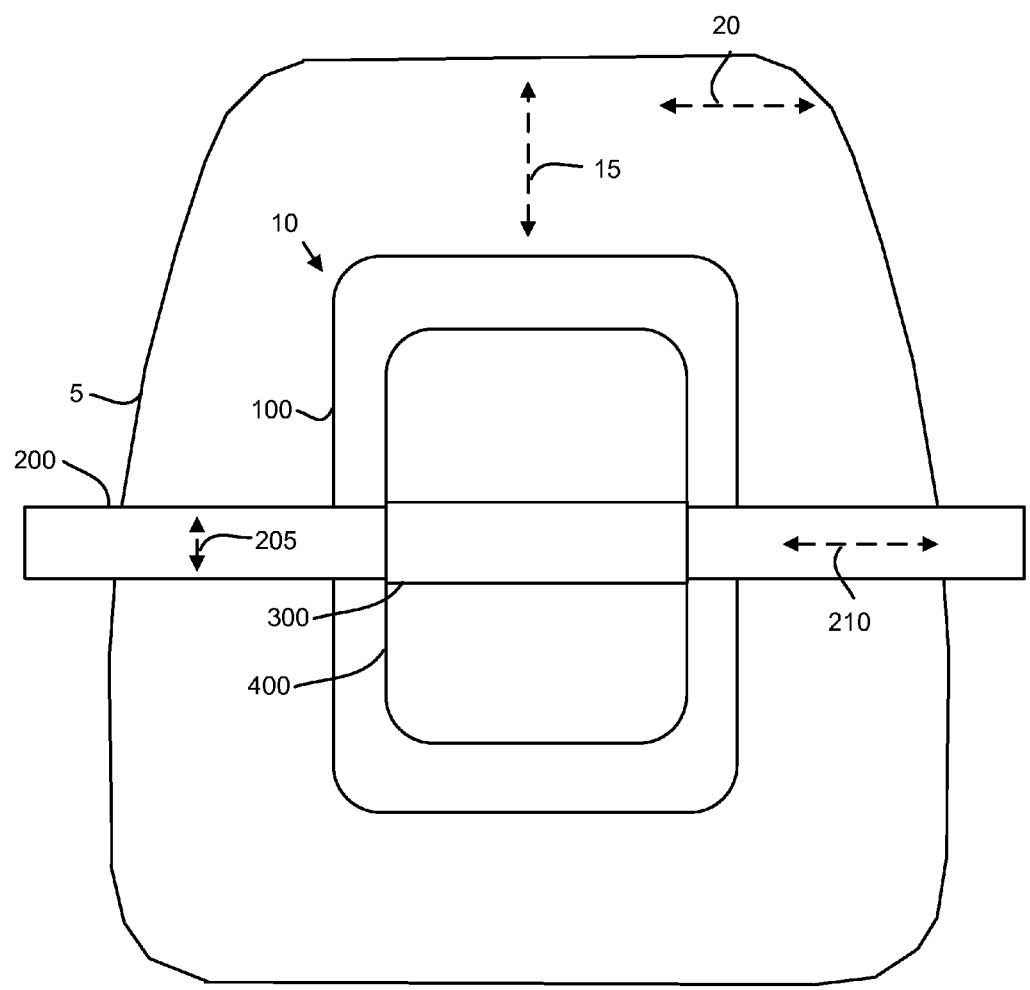
FIG. 1 is a front-view drawing illustrating one embodiment of a self-adjustable, self-ligating orthodontic bracket mounted on a tooth.

FIG. 1 is a front-view drawing illustrating one embodiment of a self-adjustable, self-ligating orthodontic bracket (hereinafter "bracket") 10 mounted on a tooth 5. The bracket 10 includes a base 100, a linking body 400, a ligating clasp 300, and an archwire 200. The base 100 is bonded to the tooth 5. The base 100 may be bonded to a labial, lingual, palatal, or the like surface of the tooth 5. An orthodontist or other medical professional, hereinafter collective referred to as orthodontist, grasps the bracket 10 with tweezers or a holding instrument and positions the bracket 10 against the tooth. The base 100 of the bracket 10 is bonded to the tooth 5 as is well known to those of skill in the art.

The base 100 and linking body 400 are depicted as roughly rectangular in shape. However, embodiments may be practiced with the base 100 and/or a linking body 400 of other shapes as will be shown hereafter.

In addition, the linking body 400 is removably connected to the archwire 200. In one embodiment, the ligating clasp 300 secures the archwire 200 in physical communication with the linking body 400. The bracket 10 transfers a force from the archwire to the tooth 5. The force therapeutically adjusts a position of the tooth 5 in a mouth as is well known to those of skill in the art.

The archwire 200 includes a latitudinal axis 205 and a longitudinal axis 210. The tooth 5 includes a vertical axis 15 and a horizontal axis 20. The archwire 200 may apply a vertically directed force along the archwire latitudinal axis 205 that motivates the tooth 5 up or down along the vertical axis 15. As used herein, motivates refers to applying a force and/or moment. The archwire 200 may also apply a horizontally directed force along the archwire longitudinal axis 210 that motivates the tooth 5 left or right along the horizontal axis 20. In addition, the archwire 200 may apply other forces and moments as will be described hereafter.

Figure 2:
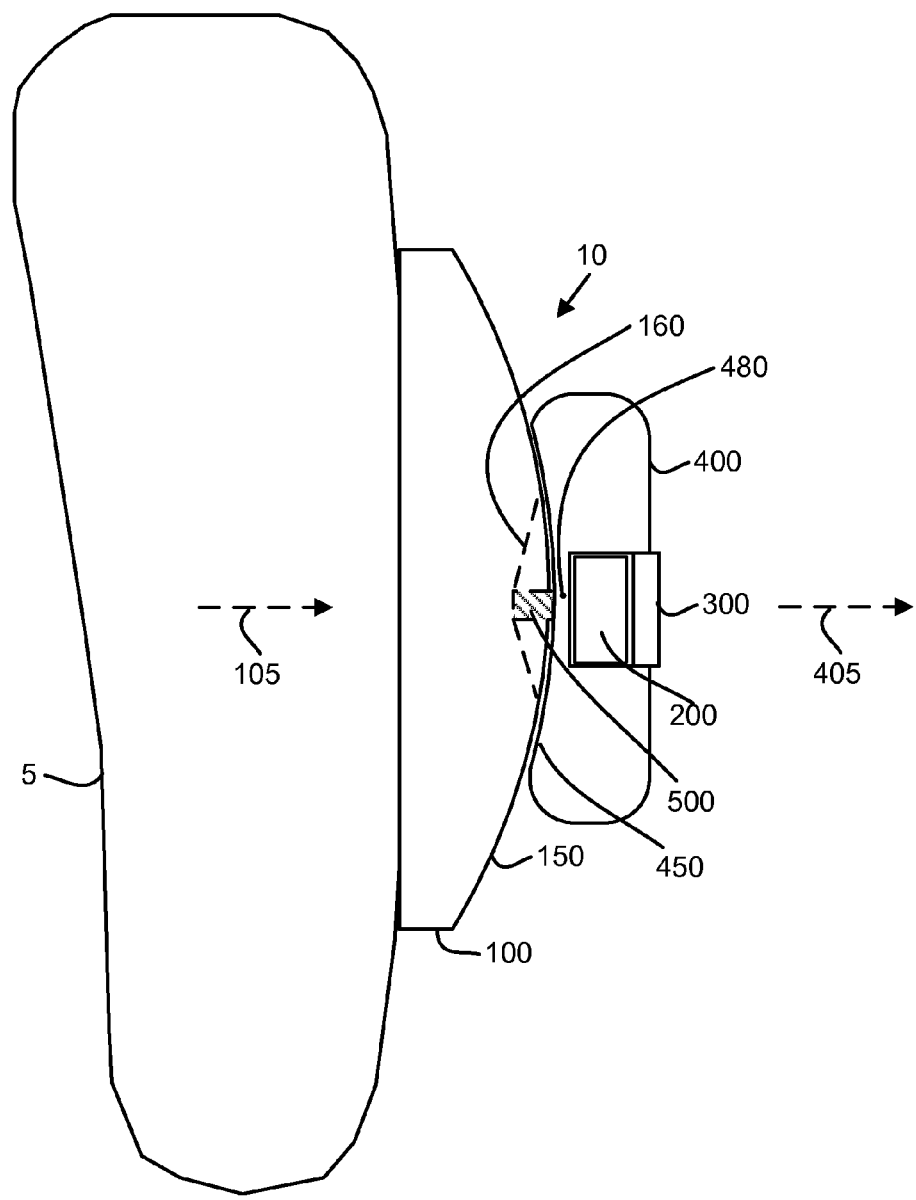
FIG. 2 is a side-view drawing illustrating one embodiment of a self-adjustable, self-ligating orthodontic bracket with a convex base mounted on a tooth.

FIG. 2 is a side-view drawing illustrating one embodiment of a bracket 10 with a convex base 100 mounted on the tooth 5. The bracket 10 may be the bracket 10 of FIG. 1. The description of the bracket 10 refers to elements of FIG. 1, like numbers referring to like elements. The linking body 400 and the base 100 are shown in a normal position. In one embodiment, a base central axis 105 of the base 100 and a body central axis 405 of the linking body 400 may be co-axial when the linking body 400 and the base 100 are in the normal position. The bracket 10 includes a connector 500.

The connector 500 connects the linking body 400 to the base 100. In one embodiment, the connector 500 applies a tension between the linking body 400 and the base 100 that motivates the linking body 400 and the base 100 towards the normal position. In one embodiment, the connector 500 is a closed coil spring. The connector 500 may be welded to the base 100 and to the linking body 400. In an alternate embodiment, the connector 500 is an elastic rod or a cable. The cable may be a twisted, multi-stranded cable.

In the depicted embodiment, the base 100 comprises a base connection 150 that is convex towards the linking body 400. The depicted embodiment further shows a linking body 400 comprising a body connection 450 that is concave. The connector 500 applies a tension between the linking body 400 and the base 100 that holds the base connection 150 in physical communication with the body connection 450 form the normal position. The linking body 400 may be repositioned relative the base 100, including but not limited to away from the base, across the curve of the base connection 150, and all rotations relative to the base 100.

In one embodiment, the connector 500 is connected to the base 100 and the linking body 400. In the depicted embodiment, the connector 500 is disposed in a base connection depression 160. The base connection depression 160 is shown as a cutaway rendering.

Figure 3:
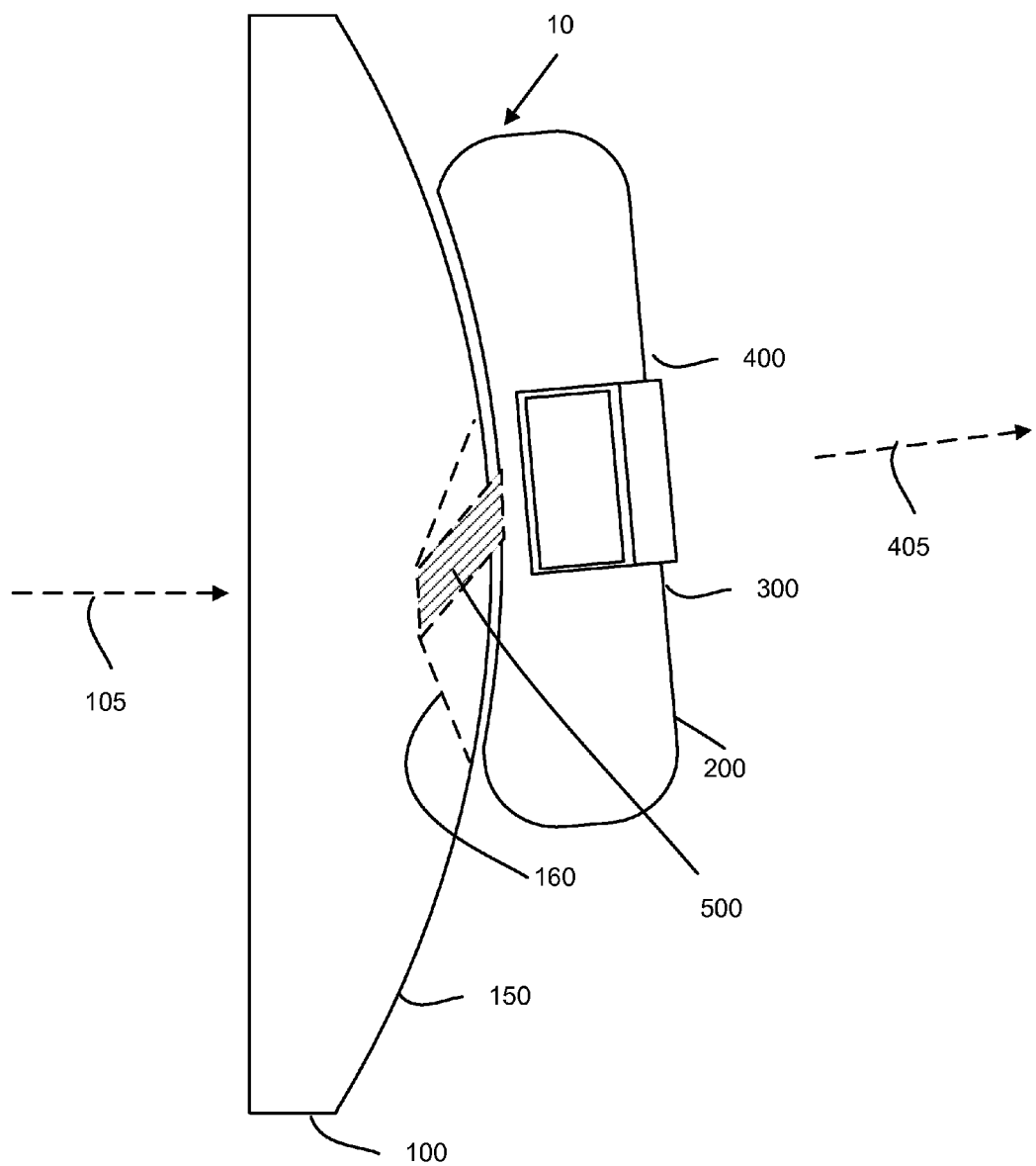
FIG. 3 is a side-view drawing illustrating one embodiment of a repositioned self-adjustable, self-ligating orthodontic bracket.

FIG. 3 is a side-view drawing illustrating one embodiment of a repositioned bracket 10. The bracket 10 is the bracket of FIG. 2. The description of the bracket 10 refers to elements of FIGS. 1-2, like numbers referring to like elements. The linking body 400 and the base 400 are depicted as positioned to an initial position from the normal position of FIG. 2. An orthodontist may position the linking body 400 and the base 100 so that the archwire 200 applies a force to the tooth 5 to reposition the tooth 5 to a desired new position and/or orientation within a dental arch.

The connector 500 applies a tension between the linking body 400 and the base 100 motivating the linking body 400 and the base 100 toward the normal position. In one embodiment, the tension maintains physical communication between the base 100 and the linking body 400. The connector 500 may stretch to an increased length as the linking body 400 and base 100 are positioned to the initial position. The stretching of the connector 500 may increase the tension between the linking body 400 and the base 100.

In one embodiment, the connector 500 is selected from an elastic high resilience metal alloy, an elastic rubber, a rubber metal, any rubber, elastomeric material, or the like material that may apply a tension. In addition, the connector 500 can be made of a metal coil spring such as a stainless steel coil spring. The tension of stretched connector may be a dynamic tension that changes with a length of the connector 500. The tension of the connector 500 may increase linearly as the connector 500 is stretched. Alternatively, the tension of the connector 500 may increase non-linearly as the connector 500 is stretched.

As the tooth 5 is repositioned in response to the force, the tension of the connector 500 may self-adjust the bracket 10 and reposition the linking body 400 and the base 100 to a second position. The second position may be along an arc between the initial position and the normal position. In one embodiment, the tension of the connector 500 between the linking body 400 and the base 100 motivates the linking body 400 and the base 100 toward the normal position, further motivating the tooth 5 toward the new position.

The self-adjustment of the bracket 10 allows the bracket 10 and archwire 200 to continue to apply a desired force to the tooth after the tooth 5 is repositioned. Thus the bracket 10 and archwire 200 may require fewer adjustments by the orthodontist to correct the position of the tooth 5. By self adjusting in response to the moment, the bracket 10 may also prevent damage and/or injury to the tooth 5 if the archwire 200 provides an excessive force to the tooth 5.

During orthodontic treatment, the teeth 5 on the dental arc of the mouth are in different states of leveling, alignment rotations, and repositioning. However, one archwire 200 is used to motivate all brackets 10, so moments from the archwire 200 are transmitted to all teeth 5. In the past, brackets were tightly coupled to the archwire, and so the brackets transferred all forces and/or moments directly from the archwire to the tooth. Teeth 5 that were more mal-positioned on a dental arch typically received a stronger force and/or moment from the archwire. Unfortunately, this stronger moment can be painful and/or damage a tooth 5 and/or affect an orthodontic movement.

In the embodiments described herein, the force and/or moment applied by the archwire 200 to the linking body 400 may displace the linking body 400 from a normal position relative to the base 100, such as is shown in FIG. 2, to an initial position relative to the base 100, such as shown in FIG. 3. In one embodiment, the linking body 400 moves to the initial position if the force and/or moment of the archwire 200 overcomes the tension value of the connector 500, stretching the connector 500.

As a result of the connector 500 being stretched to the initial position, the connector 500 applies an added tension to the linking body 400 and the base 100, further motivating the linking body 400 and the base 100 toward the normal position and so motivating the tooth 5 with the desired orthodontic movement since the tooth 5 is tightly bonded to the base 100. This extra tension of the connector 500 is transmitted through the base 100 of the bracket 10 to the tooth 5, moving the tooth 5. As a result, the base 100 moves with the tooth 5 as the tooth 5 is repositioned by the orthodontic movement.

In one embodiment, movement of the tooth 5 and the tension repositions the linking body 400 and the base 100 to a second position. In the second position, the connector 500 may continue to apply tension so that the bracket 10 self-adjusts and continues to move the tooth 5. Thus the bracket 10 may continuously adjust the moment applied to the tooth 5 throughout the movement of the tooth 5.

The second position may be the normal position. In one embodiment, the base central axis 105 and the body central axis 405 are co-axial in the normal position. In one embodiment a device including but not limited to a coil spring, a rubber band, and the like applies a force to the linking body 400.

Table 1 summarizes one embodiment of forces needed for movement of tooth 5. The forces are typically applied relative to a center of resistance of the tooth 5. The forces are measured in grams, such as grams with an acceleration of one gravity. The force required to move the tooth 5 differs from tooth 5 to tooth 5, depending on the resistance of each tooth 5, and the desired orthodontic movement for each tooth 5.

Table 1

| Orthodontic Movement Type | Force Needed (Grams) | |
| --- | --- | --- |
| | Front Teeth | Back Teeth |
| Vertically Directed Movement (Intrusion) | 10 | 20 |
| Vertically Directed Movement (Extrusion) | 35 | 60 |
| Tipping Movement | 35 | 60 |
| Rotation Movement | 35 | 60 |
| Translation or Bodily Movement | 70 | 120 |
| Orthodontic Torque | 50 | 100 |

The vertically directed movement force is a vertical force such as up or down. In addition, the vertically directed movement force may by intrusive, motivating a tooth 5 into a socket, or extrusive, motivating a tooth 5 out of the socket. The horizontally directed movement force is a horizontal force such as to the left or right, front or back, or a rotation of the tooth 5 along its longitudinal vertical axis 15. The orthodontic tipping movement rotates an end of the tooth 5 about a center of rotation of the tooth 5 and typically the crown of the tooth 5 moves towards the direction of the applied force and the end of the root of the tooth 5 moves in an opposite direction from the applied force.

The orthodontic rotation movement rotates the tooth 5 about the vertical longitudinal axis 15 of the tooth 5. The orthodontic translation or bodily movement force is a force that passes from the center of resistance of the tooth 5 causing the translation or bodily movement in which every part of the tooth 5 moves in the direction of the applied force for the same distance of movement, such as towards or away from an neighboring tooth 5. The orthodontic torque movement is a movement achieved by applying a moment on the tooth such as twisting an archwire 200 around the archwire longitudinal axis 210, rotating the bracket 10 and rotating one end of the tooth 5, typically a root, about the other end of the tooth 5, typically the crown.

In one embodiment, the surfaces of the body connection 450 and the base connection 150 are selected such that the static friction between the body connection 450 in the base connection 150 is low, so that body connection 450 moves easily relatively to the base connection 450. In case of a high static friction or increased static friction between surfaces 150 and 450 due to food trapping or erosion of the surfaces 150 and 450 during treatment or due to other factors, the added static friction will increase the tension required for the connector 500 to apply between the base 100 and the linking body 400.

Figure 4:
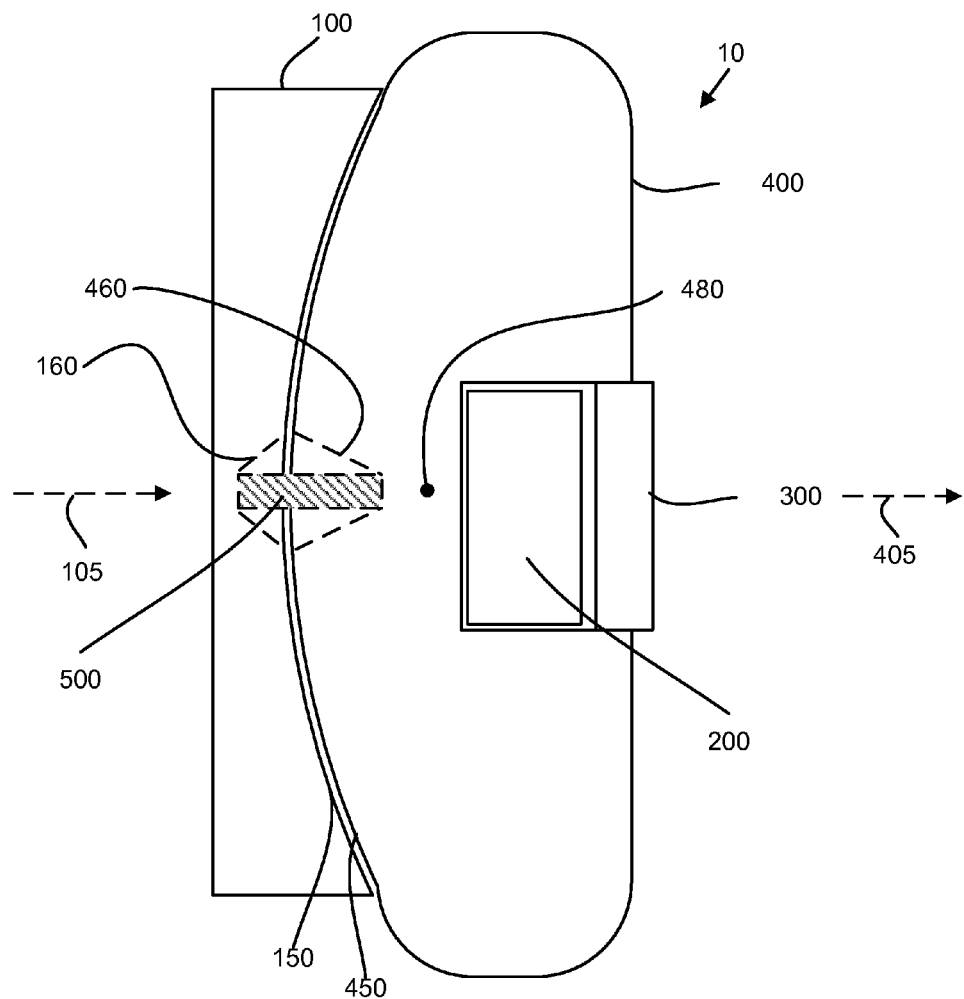
FIG. 4 is a side-view drawing illustrating one embodiment of a self-adjustable, self-ligating orthodontic bracket with a concave base.

FIG. 4 is a side-view drawing illustrating one embodiment of a bracket 10 with a concave base connection 150. The bracket 10 is the bracket 10 of FIG. 1. The description of the bracket 10 refers to elements of FIGS. 1-3, like numbers referring to like elements. The linking body 400 and the base 100 of the bracket 10 are shown in a normal position.

In the depicted embodiment, the base 100 includes a concave base connection 150. The concave base connection 150 conforms to a convex body connection 450. In one embodiment, the linking body 400 may rotate about a linking body centroid 480 so that the body connection 450 is repositioned relative to the base connection 150 to other positions.

The connector 500 is depicted disposed within a base connection depression 160 and a body connection depression 460. The base connection depression 160 and the body connection depression 460 are shown in a cutaway rendering. The base connection depression 160 and the body connection depression 460 may allow the connector to be disposed at an angle to the base central axis 105 so that the linking body 400 may be repositioned relative to the base 100. As the connector 500 is extended, the connector 500 exerts an increased tension to motivate the linking body 400 and the base 100 toward the normal position.

Figure 5:
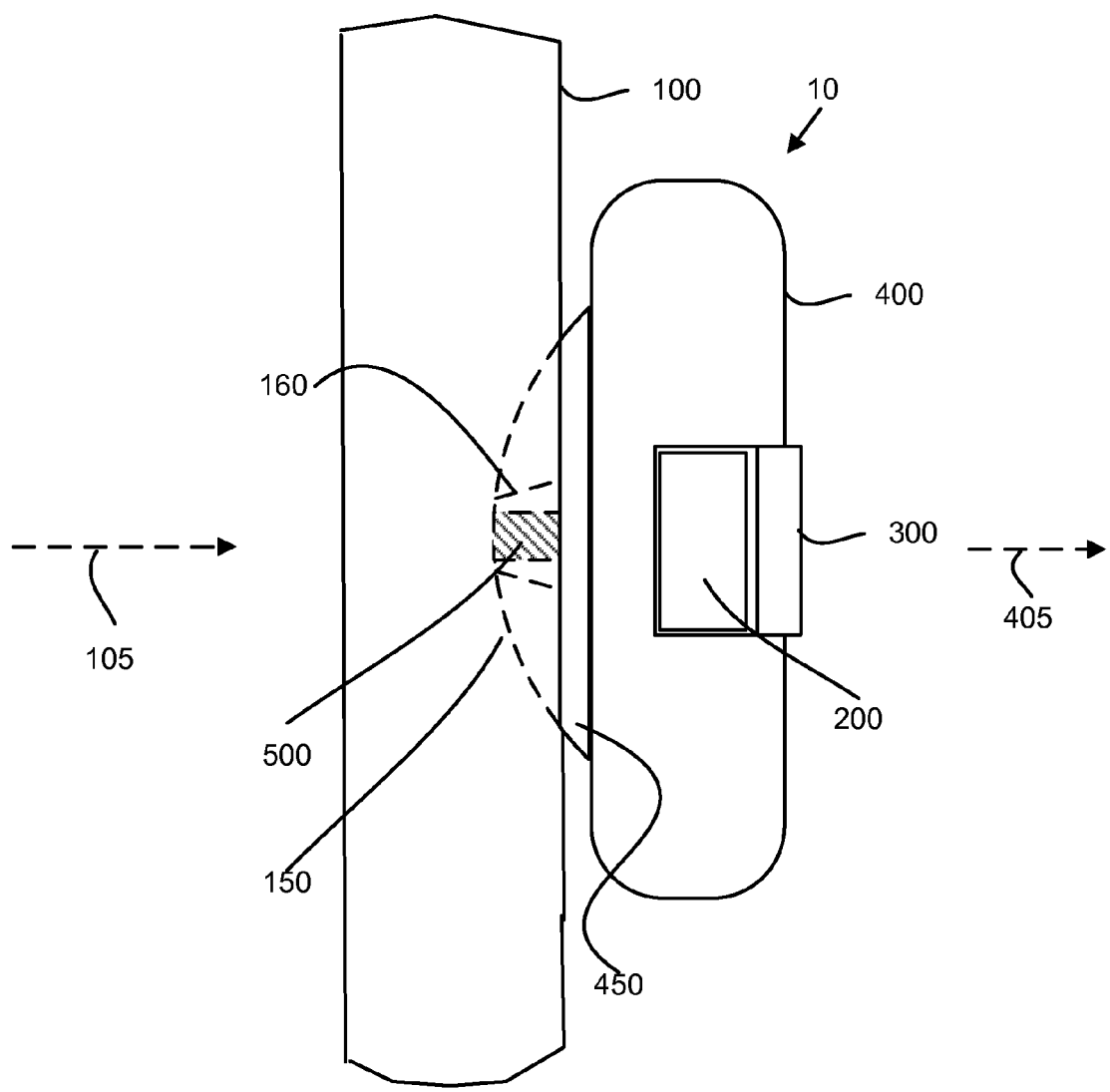
FIG. 5 is a side-view drawing illustrating one embodiment of a self-adjustable, self-ligating orthodontic bracket with a concave base connection.

FIG. 5 is a side-view drawing illustrating one embodiment of a bracket 10 with a concave base connection 160. The bracket 10 may be the bracket 10 of FIG. 1. The description of the bracket 10 refers to elements FIGS. 1-4, like numbers referring to like elements. In the depicted embodiment, the body connection 450 is a convex protrusion, rendered partially in cutaway. In addition, the base connection 150 is depicted as a concave depression rendered in cutaway. The base depression 160 and connector are also depicted in cutaway.

Figure 6:
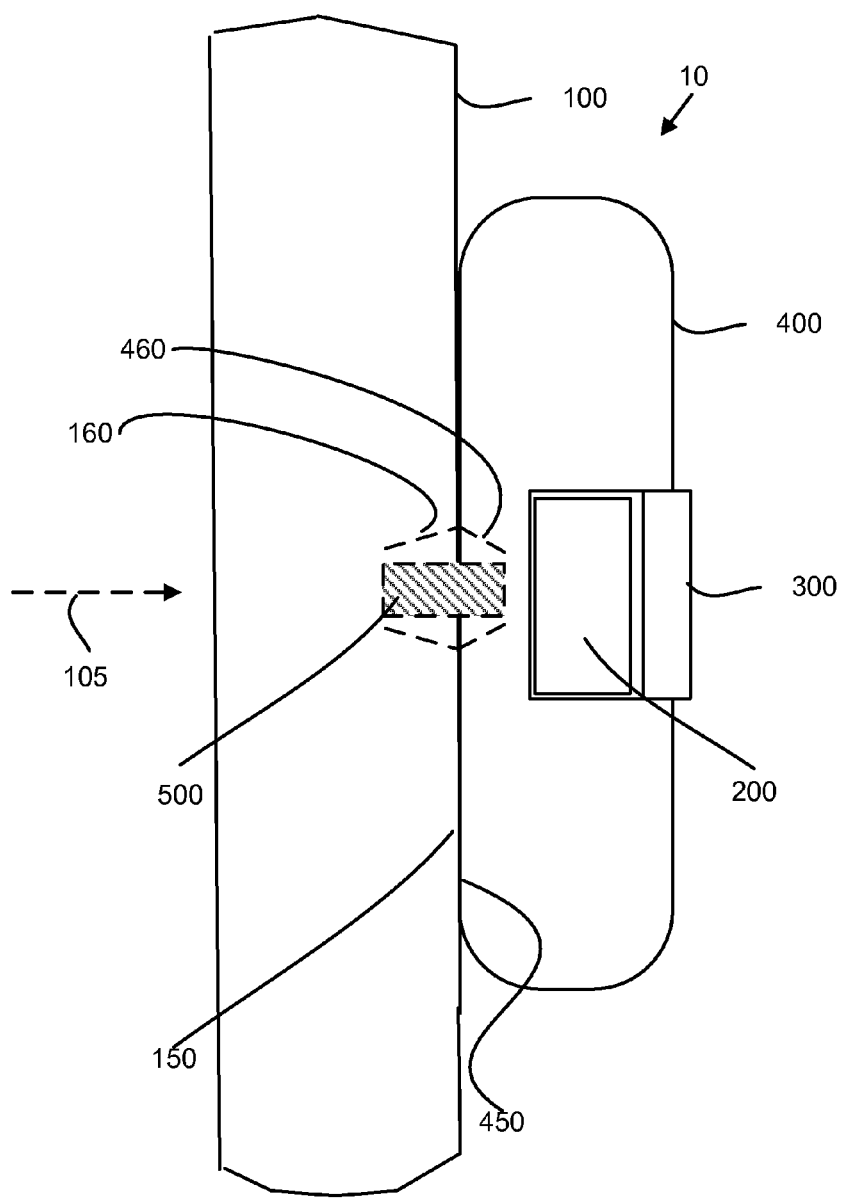
FIG. 6 is a side-view drawing illustrating one embodiment of a self-adjustable, self-ligating orthodontic bracket with a planar base connection and a planar body connection.

FIG. 6 is a side-view drawing illustrating one embodiment of a bracket 10 with a planar base connection and a planar body connection. The bracket 10 may be the bracket 10 of FIG. 1. The description of the bracket 10 refers to elements of FIGS. 1-5, like numbers referring to like elements. The linking body 400 and the base 100 are depicted in a normal position.

In the depicted embodiment, the base connection 150 and the body connection 450 are planar. As a result, the linking body 400 is constrained to move horizontally and/or vertically relative to the base connection 150.

Figure 7:
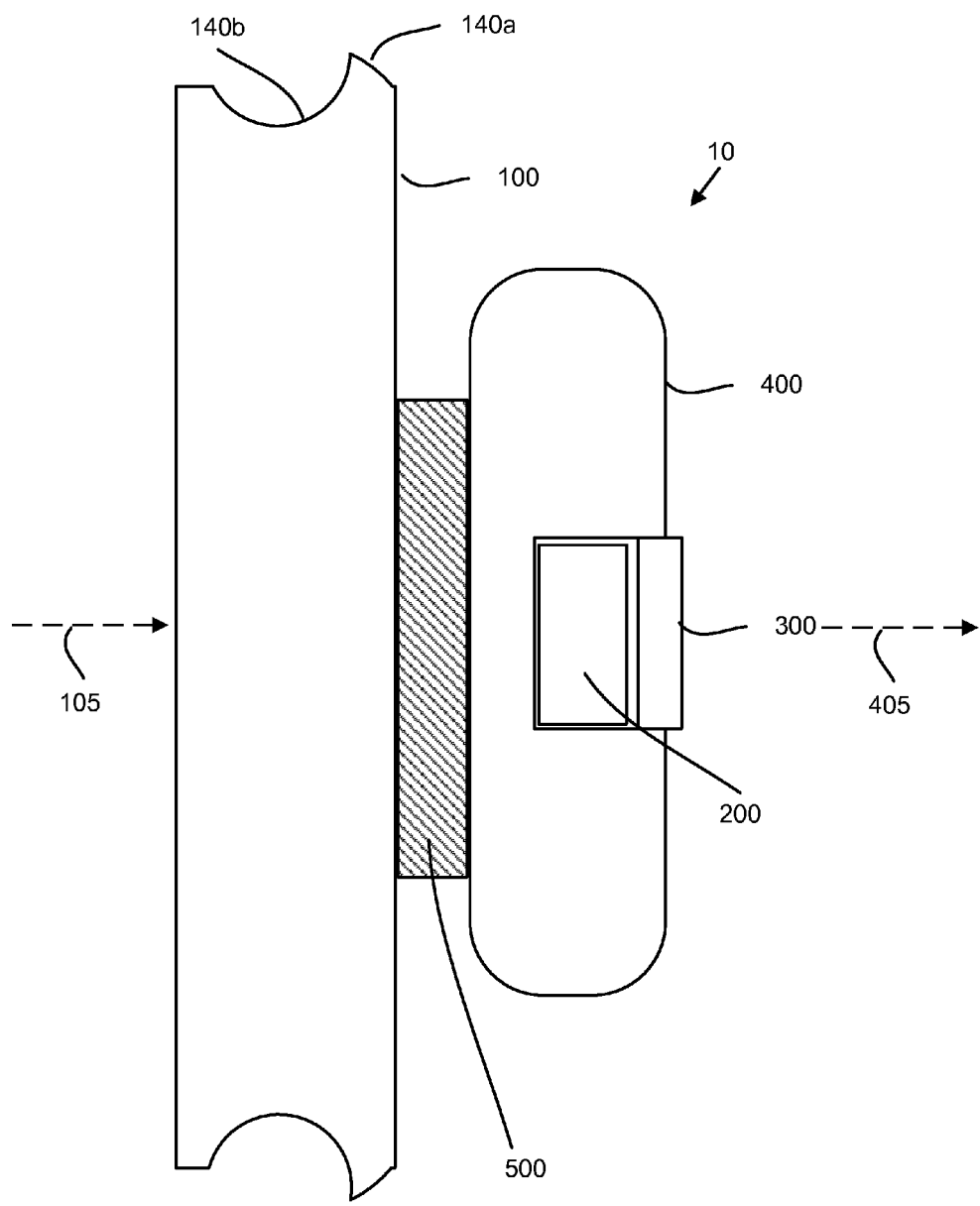
FIG. 7 is a side-view drawing illustrating one alternate embodiment of a self-adjustable, self-ligating orthodontic bracket.

FIG. 7 is a side-view drawing illustrating one alternate embodiment of a bracket 10. The bracket 10 may be the bracket 10 FIG. 1. The description of the bracket 10 refers to elements of FIGS. 1-6, like numbers referring to like elements.

In the depicted embodiment, the base 100 and the linking body 400 are not in physical communication. The position of the linking body 400 relative to the base 100 is maintained by a tension applied by the connector 500.

The linking body 400 and the base 100 are shown in a normal position. If the linking body 400 and base 100 are repositioned to another position, the connector 500 may motivate the linking body 400 and the base 100 toward the normal position. A base rim 140 may have a base lip 140a and/or or a circumferential base groove 140b to hold the bracket when bonding and/or debonding.

Figure 8:
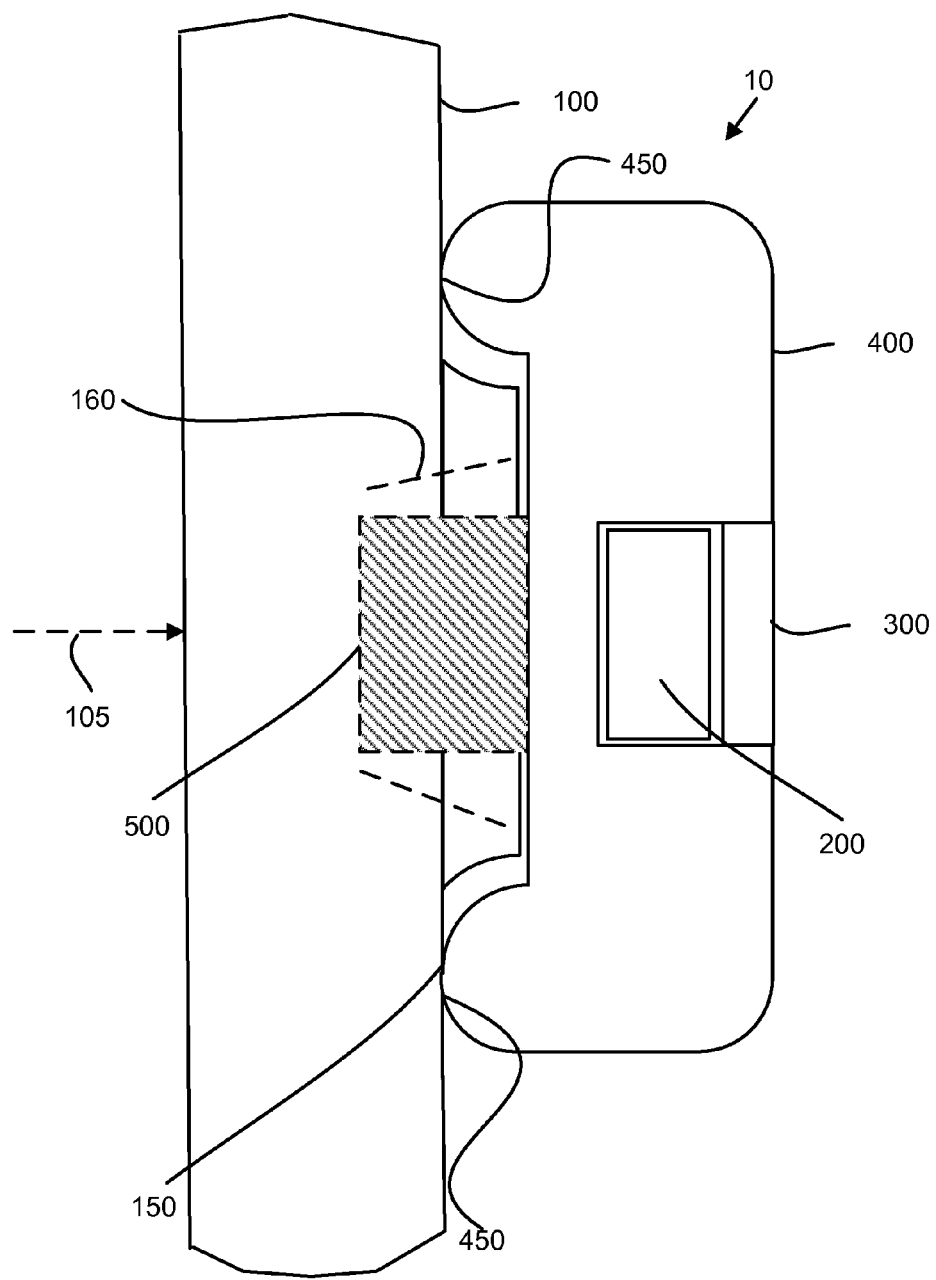
FIG. 8 is a side-view drawing illustrating another alternate embodiment of a self-adjustable, self-ligating orthodontic bracket.

FIG. 8 is a side-view drawing illustrating another alternate embodiment of a bracket 10. The bracket 10 may be the bracket 10 FIG. 1. The description of the bracket 10 refers to elements of FIGS. 1-7, like numbers referring to like elements.

In the depicted embodiment, the base connection 150 is a planar surface. The body connection 450 may be an annular protrusion from the linking body 400. The linking body 400 may move horizontally and/or vertically across the base connection 150.

In the depicted embodiment, the body 100 further includes a restraining protrusion 190. The restraining protrusion 190 may limit the movement of the linking body 400 relative to the base 100. In one embodiment, the restraining protrusion is integrated with the body 100.

Figure 9:
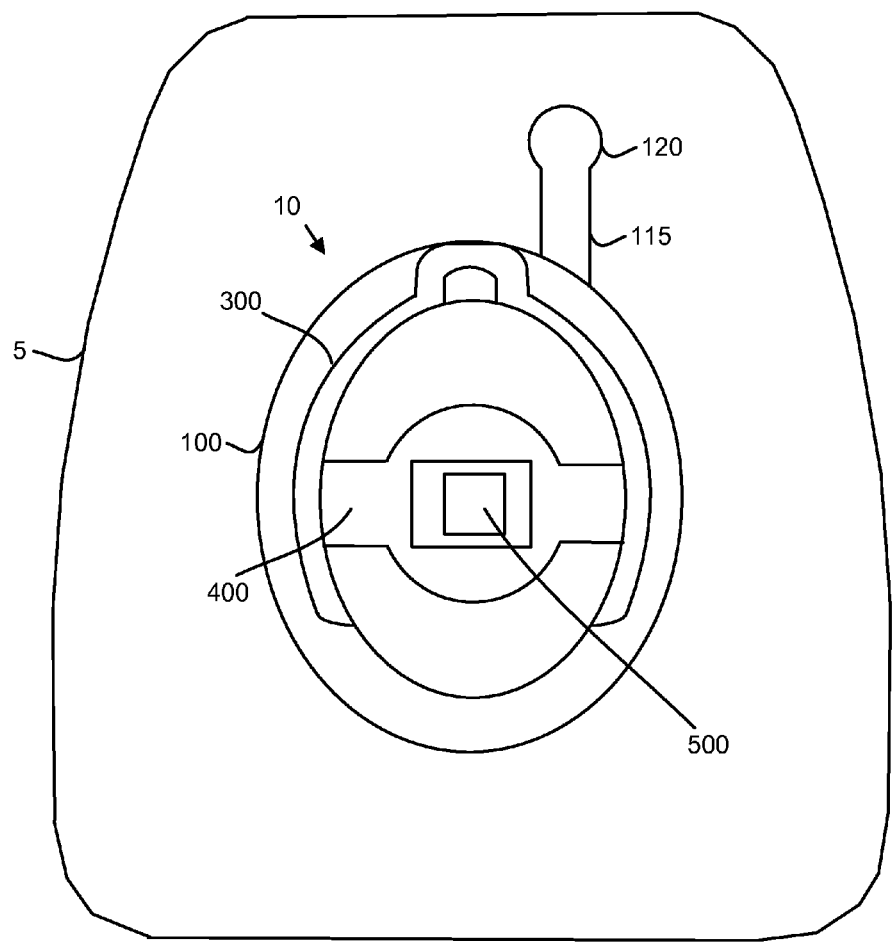
FIG. 9 is a front-view drawing illustrating one embodiment of a self-adjustable, self-ligating orthodontic bracket mounted on a tooth.

FIG. 9 is a front-view drawing illustrating one embodiment of the bracket 10 mounted on the tooth 5. The bracket may be the bracket 10 of FIG. 1. The description of the bracket 10 refers to elements of FIG. 1-8, like numbers referring to like elements. The base 100 includes a hook 115 with a hook ball 120. In one embodiment, the linking body 400 and the base 100 are in a normal position.

The connector 500 connects the linking body 400 to the base 100. The connector 500 applies a tension between the linking body 400 and the base 100 motivating the linking body 400 and the base 100 toward a normal position. Additional details of the bracket 10 are shown hereafter.

Figure 10:
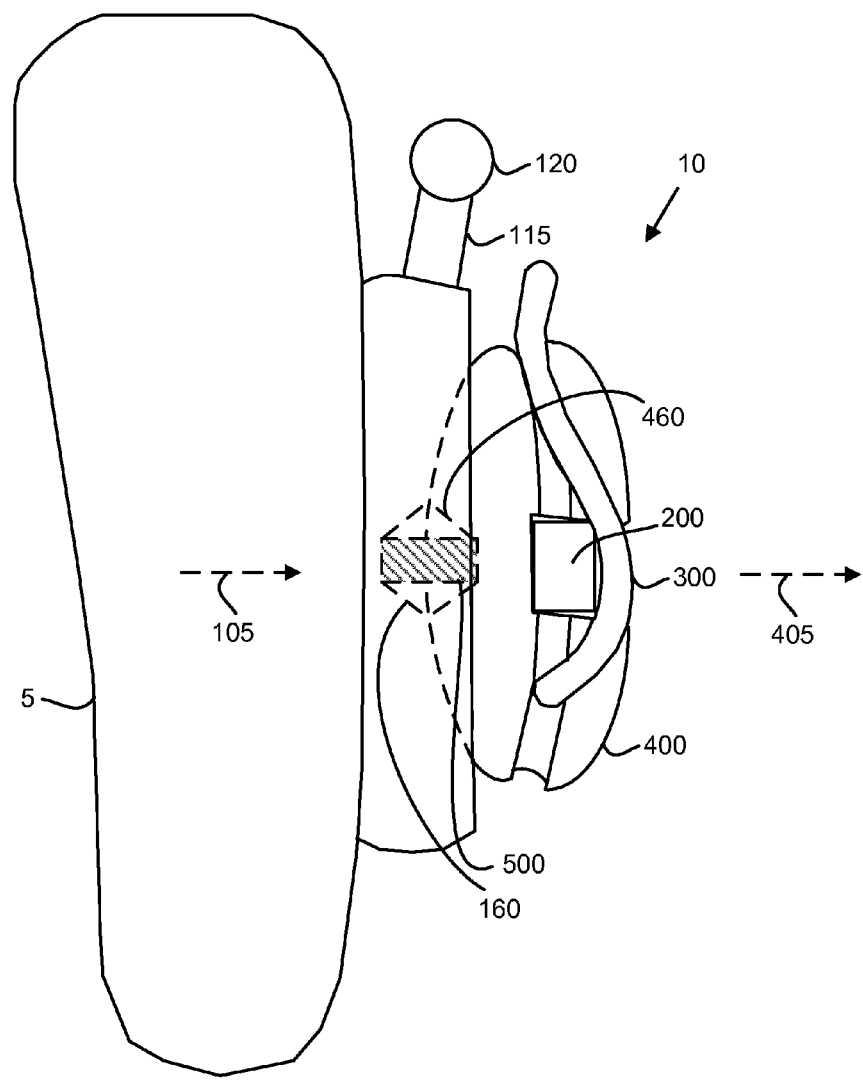
FIG. 10 is a side-view drawing illustrating one embodiment of a self-adjustable, self-ligating orthodontic bracket mounted on a tooth.

FIG. 10 is a side-view drawing illustrating one embodiment of the bracket 10 of FIG. 9 mounted on the tooth 5. The description of the bracket 10 refers to elements of FIGS. 1-9, like numbers referring to like elements. In one embodiment, the linking body 400 and the base 100 are in a normal position. The archwire 200 is depicted secured to the linking body 400 by the ligating clasp 300.

The archwire 200 may have a round cross section. Alternatively, the archwire 200 may have a rectangular cross section. The archwire 200 may be formed of a nickel titanium alloy. Alternatively, the archwire 200 may be formed of stainless steel and/or other metal alloys.

The ligating clasp 300 is positioned in a closed position, removably securing the archwire 200 against the linking body 400. When secured to the linking body 400, the archwire transfers a force through the linking body 400, including but not limited to through the connector 500, to the base 100 and to the tooth 5.

The archwire 200 is shaped to motivate the tooth 5 to a desired position leveling, alignment, and orientation of the first position. The archwire 200 may apply moments and/or forces through the bracket 10 to the tooth 5 to reposition realign, relevel, and reorient the tooth 5 as is well known to those of skill in the art.

Figure 19:
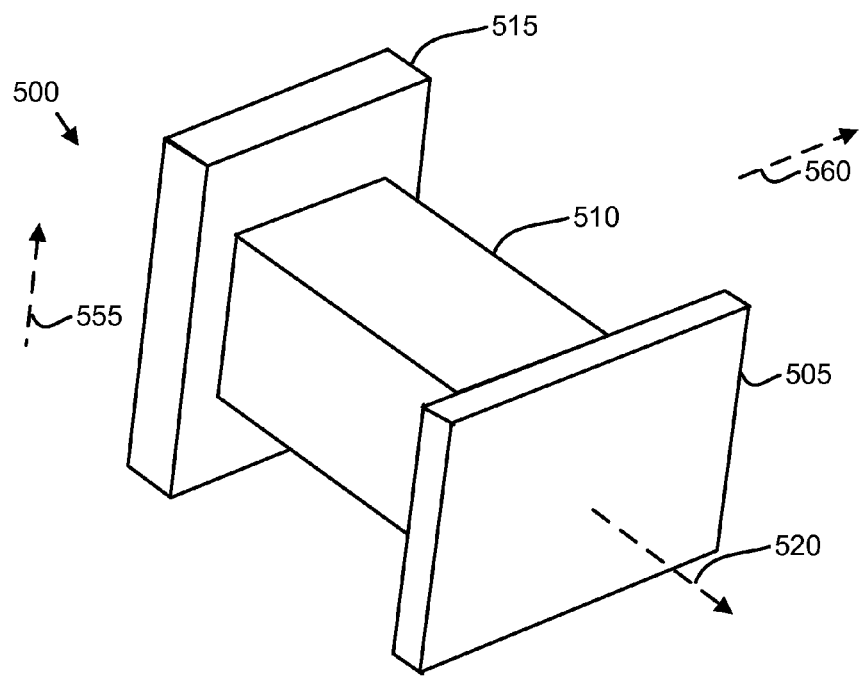
FIG. 19 is a perspective-view drawing illustrating one embodiment of a connector.

The base central axis 105 and the body central axis 405 are also shown. The base central axis 105 and the body central axis 405 may be co-axial in the normal position. The connector central axis 520 is shown in FIG. 19.

Figure 11:
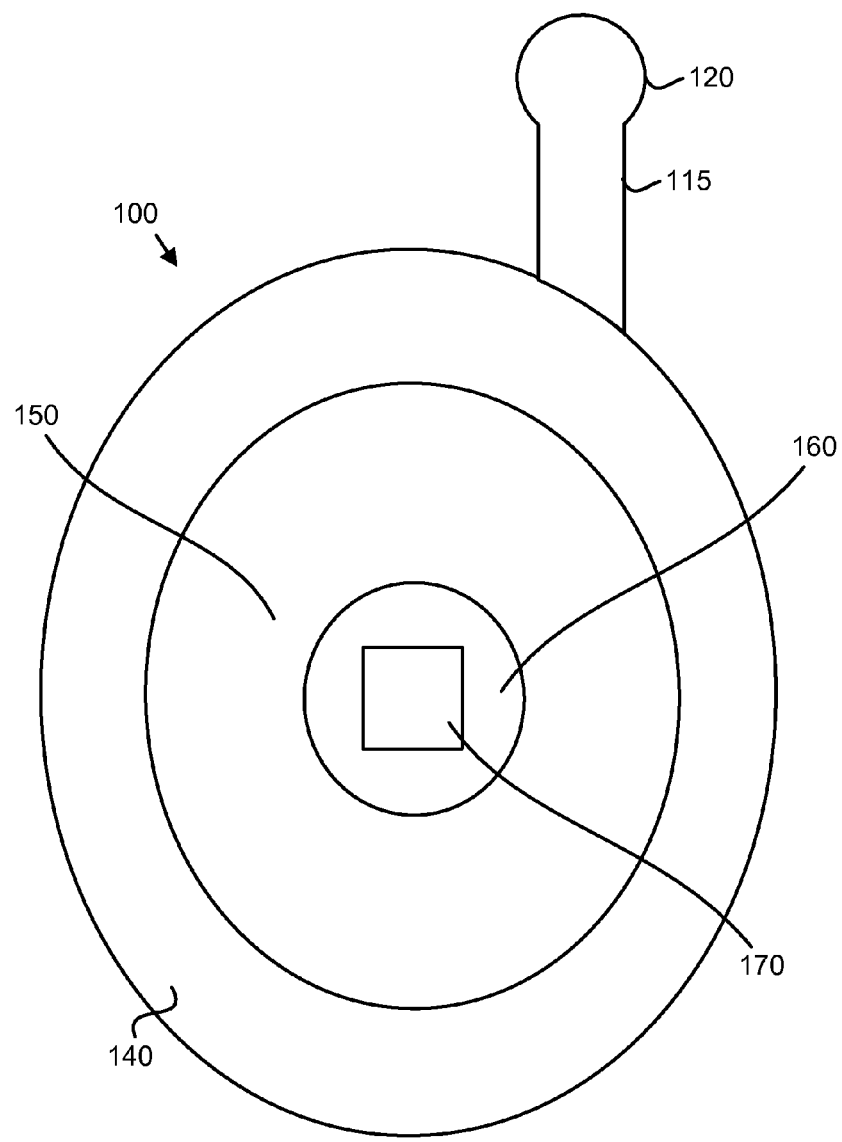
FIG. 11 is a front-view drawing illustrating one embodiment of a base.

FIG. 11 is a front-view drawing illustrating one embodiment of a base 100. The base 100 is the base 100 of FIGS. 9-10. The description of the base refers to elements of FIGS. 1-10, like numbers referring to like elements. The base 100 includes the hook 115, the hook ball 120, the base connection 150, the base connection depression 160, and a base hole 170.

The base 100 may be fabricated of a metal including but not limited to stainless steel, titanium, titanium chromium alloy, nickel titanium alloy, plastic, polycarbonate, fiberglass reinforced plastic, polyurethane, ceramic, metal reinforced ceramic including alumina and/or zirconia ceramics, epoxy resin, reinforced epoxy resin, cobalt chromium alloy, or the like. In one embodiment, the base 100 is cast. Alternatively, the base 100 may be injection molded, and/or cast using casting technique. In addition, the base 100 may be machined.

In one embodiment, the base connection 150 is a concave depression. The base connection 150 may be positioned in physical communication with a body connection 450 of the linking body 400 as will be described hereafter.

The connector 500 passes through the base hole 170. The base connection depression 160 provides clearance for the connector 500 to flex about the base central axis 105. The base connection depression 160 may be formed as an indent in the base 100 about the base hole 170 on a front side of the base 100. The base connection depression 160 may have conical shape, a bowl shape, a pyramidal shape, or the like. The base connection depression 160 may allow the connector central axis to be disposed at an angle to the base central axis 105. In one embodiment, the connector 500 may be disposed with the connector central axis at an angle of 0 to 45 degrees to the base central axis 105. In an alternate embodiment, the connector 500 may rotate about the base central axis 105.

The hook 115 and the hook ball 120 provides a connection point for orthodontic accessories including wires, springs, power elastic chains, and the like. One of skill in the art will recognize that the embodiments may employ a hook 115 and hook ball 120 and/or other grasping structure with an alternate physical configuration.

The base rim 140 may be a flat surface. Alternatively, the base rim 140 may be a beveled surface. The base rim 140 may have a base lip 140a and/or or a circumferential base groove 140b to hold the bracket when bonding or debonding. A width of the base rim 140 may vary from no width a one half the width of the base 100.

Figure 12:
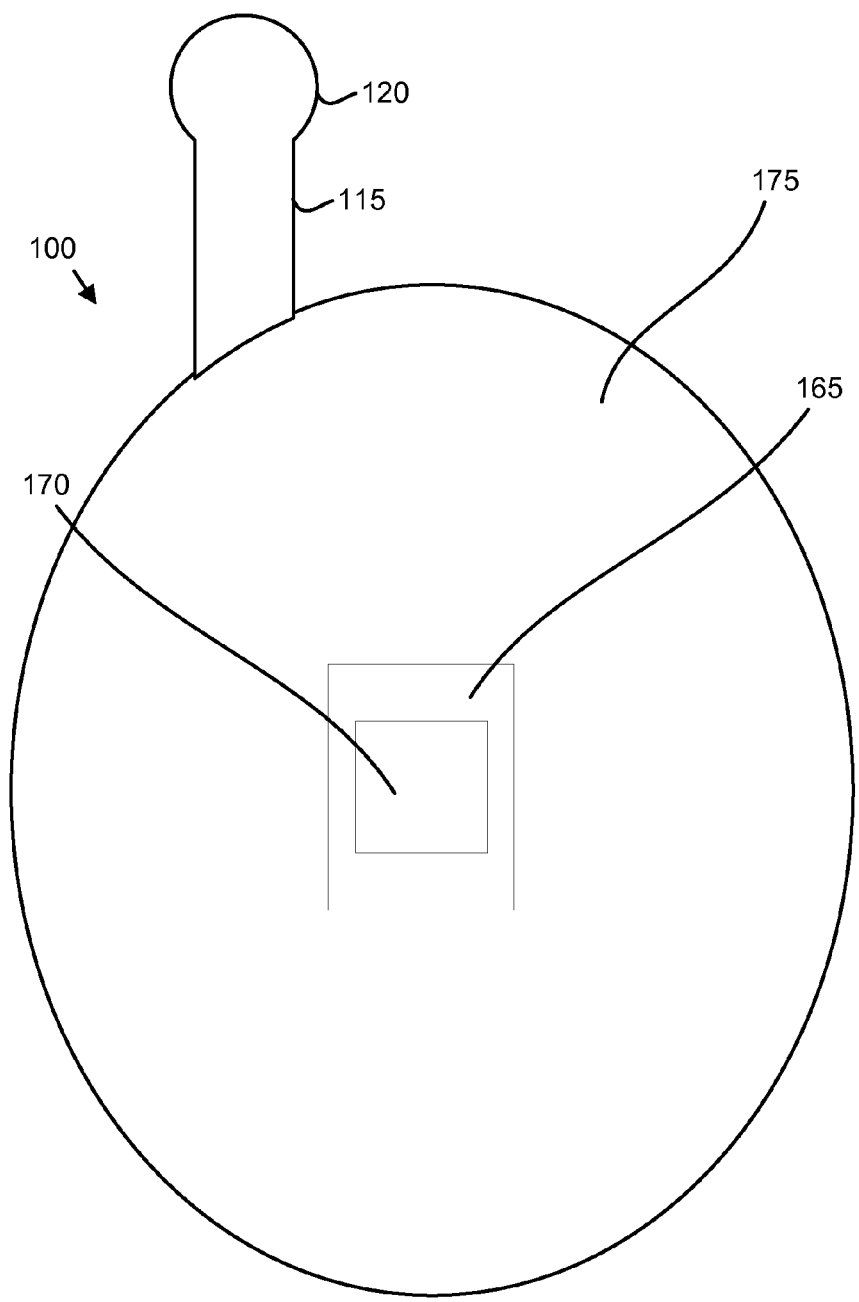
FIG. 12 is a back-view drawing illustrating one embodiment of a base.

FIG. 12 is a back-view drawing illustrating one embodiment of the base 100. The base 100 is the base 100 of FIGS. 9-11. The description of the base 100 refers to elements of FIGS. 1-11, like numbers referring to like elements. The base 100 includes a tooth face 175 and a base recess 165.

The tooth face 170 may be a flat surface. Alternatively, the tooth face 170 may have a curvature that conforms to a curvature of the tooth 5. The base recess 165 may receive a connector tail of the connector 500. The base recess 165 may be formed to conform to an anti-aliasing shape of the connector tail.

Figure 13:
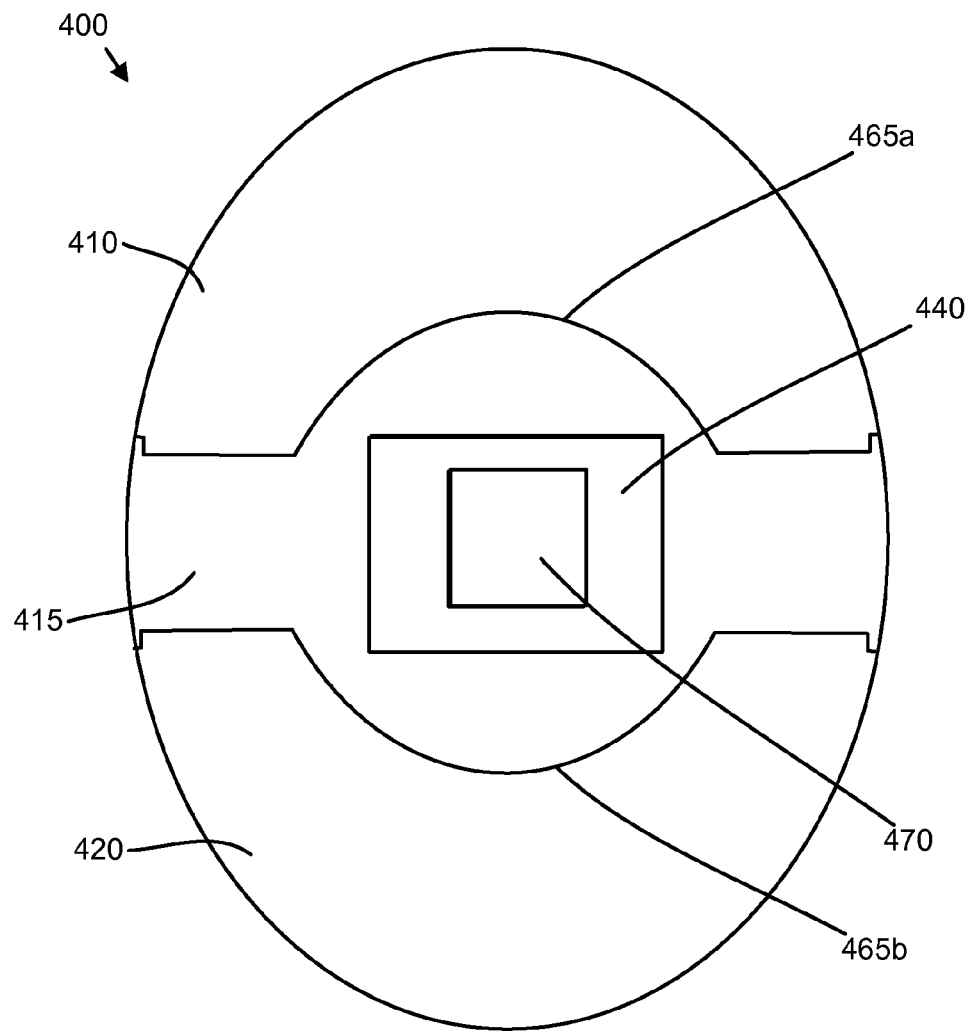
FIG. 13 is a front-view drawing illustrating one embodiment of a linking body.

FIG. 13 is a front-view drawing illustrating one embodiment of the linking body 400. The linking body 400 is the linking body 400 of FIGS. 9-10. The description of the linking body 400 refers to elements of FIGS. 1-12, like numbers referring to like elements. The linking body 400 includes a slot 415, a first ridge 410, a second ridge 420, a body hole 470, and a body recess 440.

The linking body 400 may be fabricated of a material including but not limited to stainless steel, titanium, titanium chromium alloy, nickel titanium alloy, plastic, polycarbonate, fiberglass reinforced plastic, polyurethane, a ceramic, a metal reinforced ceramic such as alumina and/or zirconia ceramics, epoxy resin, a reinforced epoxy resin, cobalt chromium alloy or the like. In one embodiment, the linking body 400 is cast. Alternatively the linking body 400 may be injection molded. In addition, the linking body 400 may be machined.

The body recess 440 may receive a connector head of the connector 500. The body recess 440 may be formed to conform to an anti-aliasing shape of the connector head.

The slot 415 may be formed between the first ridge 410 and the second ridge 420. In one embodiment, the slot 415 is made of the same material as the linking body 400. Alternatively, the slot 415 may be lined with a low friction metal alloy. The metal alloy may be added as an insert. The slot 415 receives the archwire 200. In one embodiment, the slot 415 conforms to a shape of the archwire 200. The slot 415 has a vertical wall 415a, an upper wall 415b, and a lower wall 415c.

In one embodiment, the first ridge 410 comprises a first clearance cut 465a and the second ridge 420 comprises a second clearance cut 465b. The clearance cuts 465 may provide clearance for installing the connector 500, and decrease the weight of the bracket 10. In addition, the clearance cuts 465 may reduce friction between the linking body 400 and the archwire 200.

Figure 14:
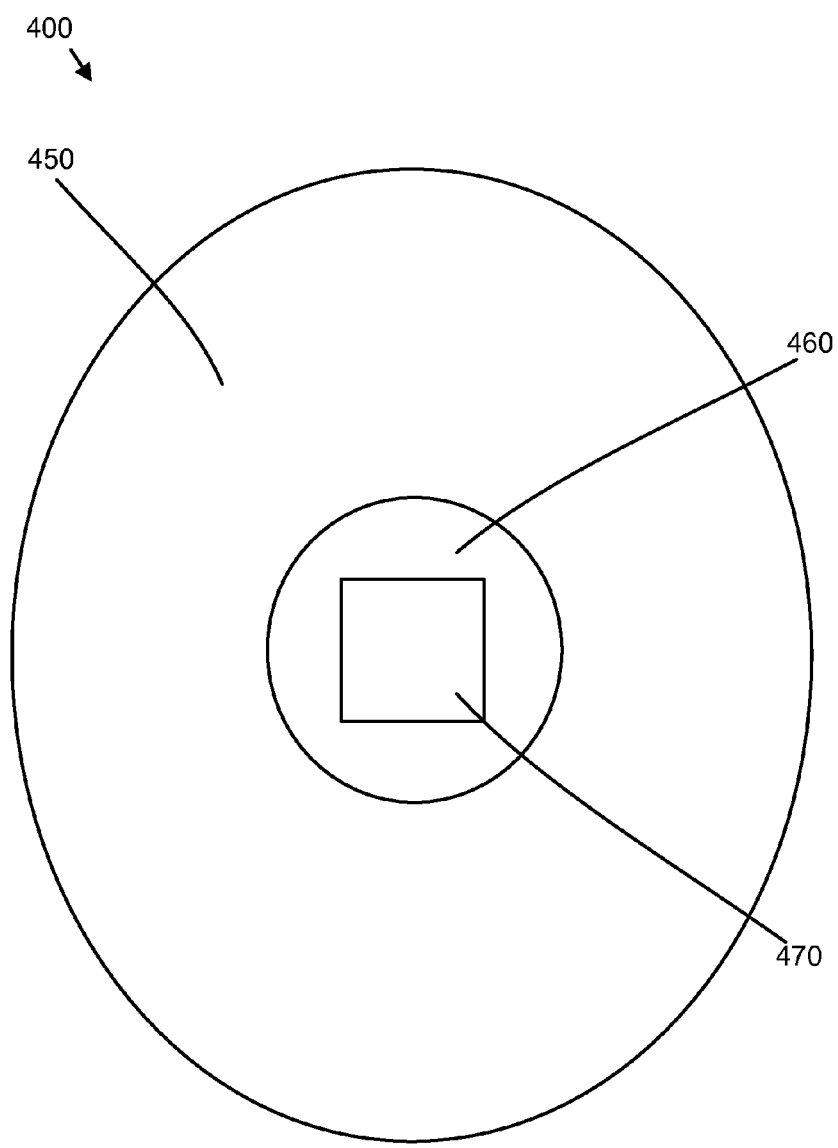
FIG. 14 is a back-view drawing illustrating one embodiment of a linking body.

FIG. 14 is a back-view drawing illustrating one embodiment of the linking body 400. The linking body 400 is the linking body 400 of FIGS. 9, 10 and 13. The description of the linking body 400 refers to elements of FIGS. 1-13, like numbers referring to like elements. The linking body 400 as depicted includes the body connection 450, the body connection depression 460, and the body hole 470.

The body connection 450 is positioned in physical communication with the base connection 150. The body connection 450 may be positioned to form an initial position with a first angle between the base central axis 105 and the linking body central axis 405.

The base connection 450 may be concave. The body depression 460 may be formed as an indentation into the linking body 400 about the body hole 470. The body depression 460 may be formed as a portion of a negative cone, a bowl, a pyramid, or the like. The body connection depression 460 may allow the connector 500 to be disposed with the connector central axis at an angle to the body central axis 405.

Figure 15:
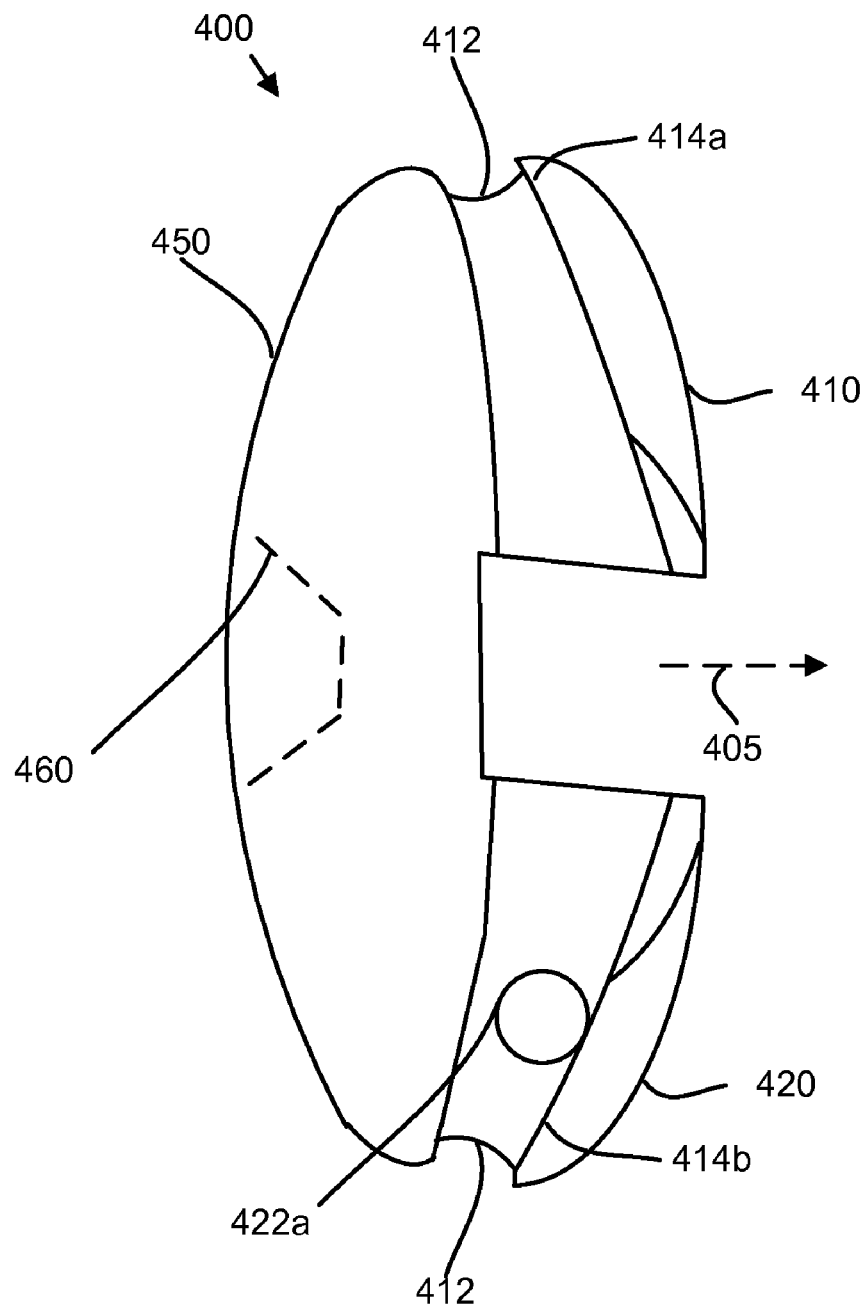
FIG. 15 is a side-view drawing illustrating one embodiment of a linking body.

FIG. 15 is a side-view drawing illustrating one embodiment of the linking body 400. The linking body 400 is the linking body 400 of FIGS. 9-10. The description of the linking body 400 refers to elements of FIGS. 1-14, like numbers referring to like elements. The linking body 400 includes a body groove 412, a lip 414, a first socket 422a, and a second socket 422b (not shown). The second socket 422b is shown as a hidden line representation in FIG. 17. The two sockets 422a and 422b may be co-axial and allow easy rotation of the ligating clasp 300. Alternatively, the sockets 422 may have different axes, and increase the tension needed to open the clasp 300.

In one embodiment, the body groove 412 encircles the linking body 400. The body groove 412 may be perpendicular to the linking body central axis 405. The body groove 412 may form a curvature with a space underneath the lip 414 to retain the ligating clasp 300. The body groove 412 may include a first lip 414a on the first ridge 410 and a second lip 414b on the second ridge 420. The two lips 414 with or without the body groove 412 may be used to fix ligating wires, elastic power chains, O-shaped elastomeric bands, and the like to the linking body 400.

In one embodiment, the body groove 412 receives orthodontic accessories. The orthodontic accessories may be used to ligate the linking body 400 to the archwire 200 as is well known to those of skill in the art. The orthodontic accessories may be selected from the group consisting of O-shaped elastomeric bands, elastic power chains, and metal ligating wires.

Figure 17:
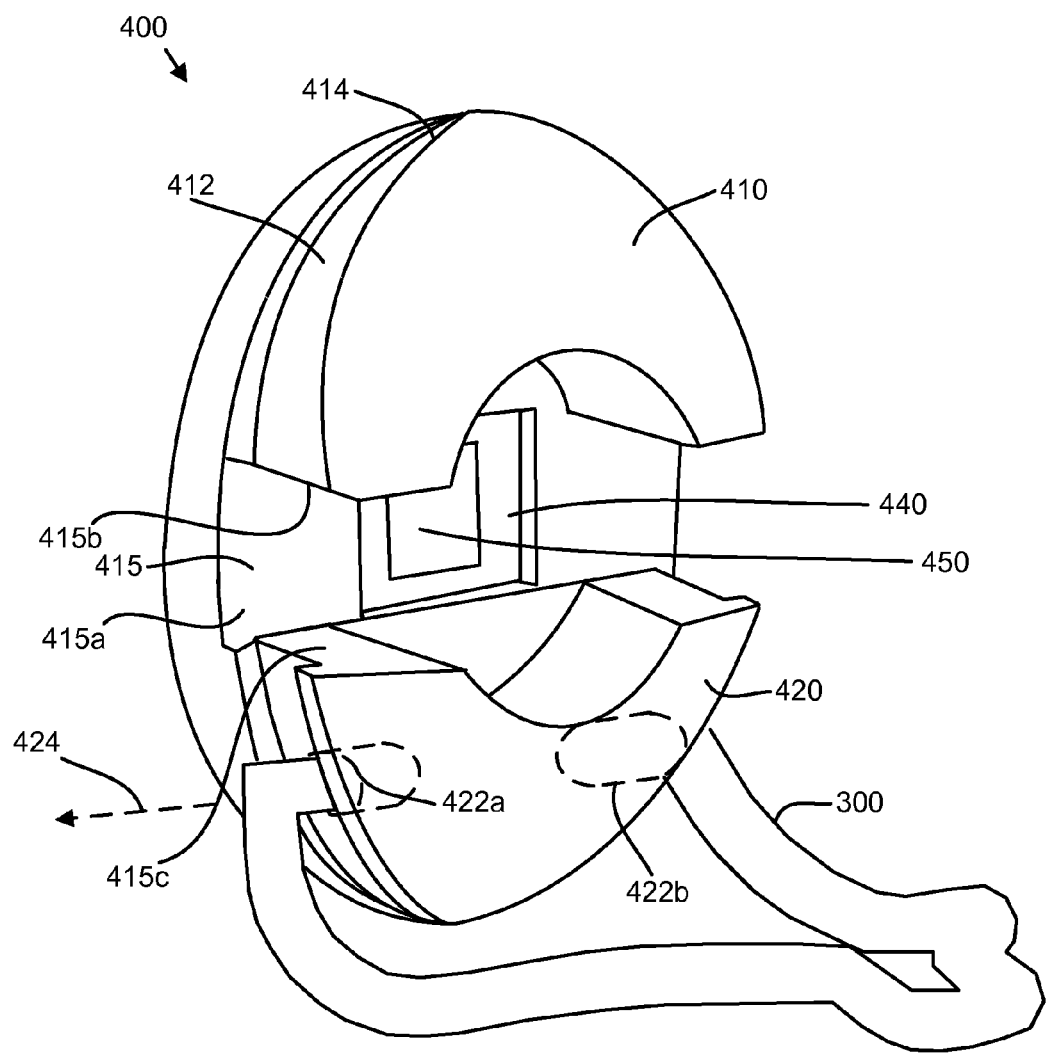
FIG. 17 is a perspective-view drawing illustrating one embodiment of a linking body with a ligating clasp in a released position.

The first socket 422a and the second socket 422b may be aligned along the socket axis shown in FIG. 17. In one embodiment, the first and second sockets 422a, b may be formed as a contiguous hole in the linking body 400 from side of the linking body 400 to another side of the linking body 400. In a certain embodiment, and the sockets 422 are used for connecting other accessories to the linking body 400.

Figure 16:
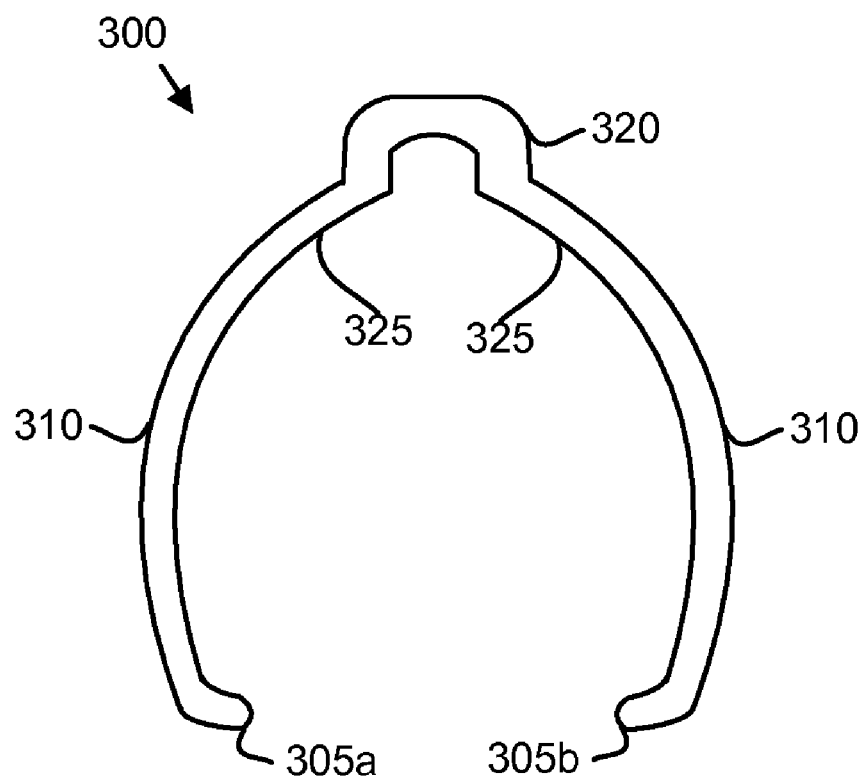
FIG. 16 is a front-view drawing illustrating one embodiment of a ligating clasp.

FIG. 16 is a front-view drawing illustrating one embodiment of the ligating clasp 300. The ligating clasp 300 is the ligating clasp of FIGS. 19-10. The description of the ligating clasp 300 refers to elements of FIGS. 1-15, like numbers referring to like elements. The ligating clasp 300 includes an arched bar 310 with a first end 305a and a second end 305b. In addition, the ligating clasp 300 may include a handle 320.

The ligating claps 300 may be formed of a flexible metal such as nickel titanium, stainless steel, and/or plastic. The ligating clasp 300 may be stamped, alternatively, the ligating clasp 300 may be injection molded. In one embodiment, the ligating clasp 300 has a curvature following a shape of the linking body 400.

The ligating clasp 300 may include a ligating portion 325. The ligating portion 325 may latch under the lip 414a to latch the linking body 400 in a latched position.

FIG. 17 is a perspective-view drawing illustrating one embodiment of a linking body 400 with the ligating clasp 300 in the released position. The linking body 400 is the linking body 400 of FIGS. 9, 10, 13, and 14. The ligating clasp 300 is the ligating clasp 300 of FIGS. 1, 2, and 7. The description of the linking body 400 and ligating clasp 300 refers to elements of FIGS. 1-16, like numbers referring to like elements.

The first end 305a of the ligating clasp 300 may be disposed in the first socket 422a of the linking body 400 and the second end 305b may be disposed in the second socket 422b of the linking body 400.

The arched bar 310 may rotate about the socket axis 424. In the depicted embodiment, the arched bar 310 is rotated to the released position. The ligating clasp 300 may be removed from the first and second sockets 422, and a new ligating clasp 300 installed in the first and second sockets 422.

Figure 18:
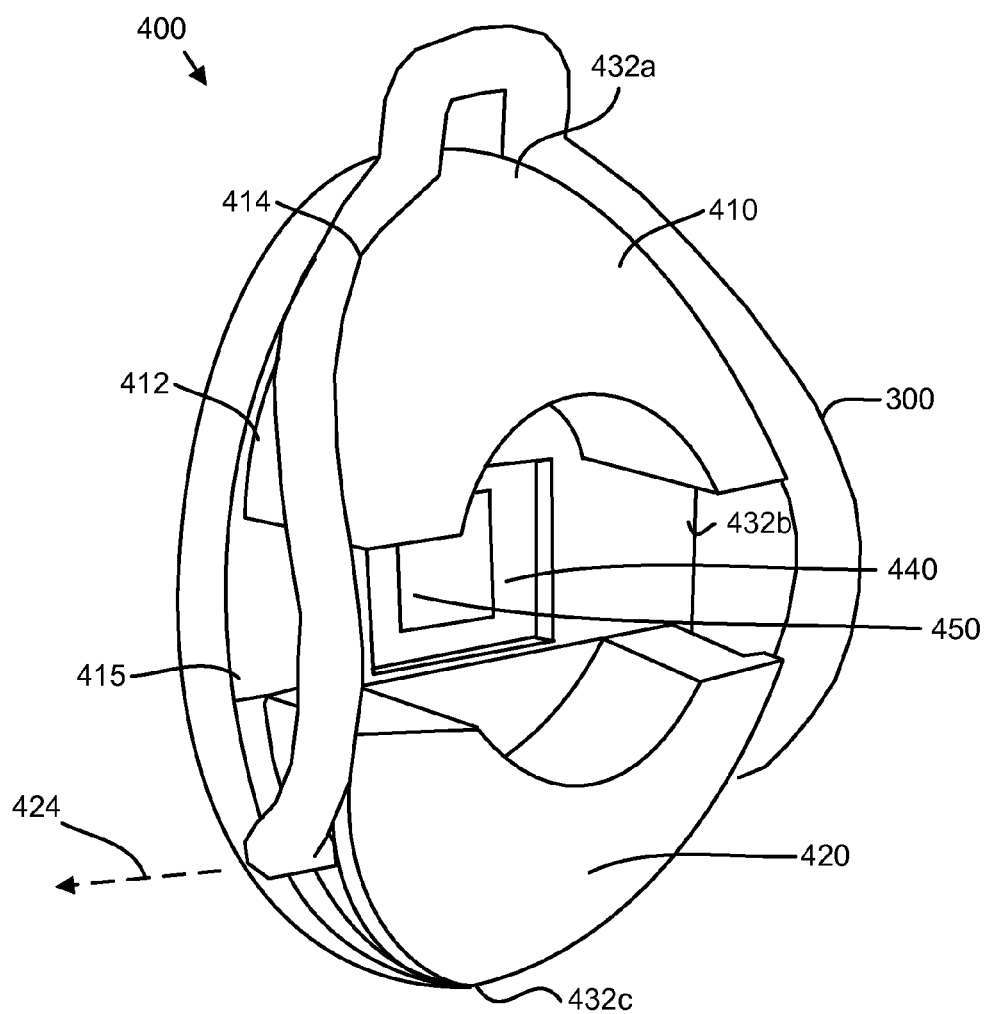
FIG. 18 is a perspective-view drawing illustrating one embodiment of a linking body with a ligating clasp in a latched position.

FIG. 18 is a perspective-view drawing illustrating one embodiment of the linking body 400 of FIG. 17 with the ligating clasp 300 in the latched position. The arched bar 310 is rotated about the socket axis 424 to the latched position. In one embodiment, the lip 414a latches the ligating portion 325 to prevent the arched bar 310 from rotating from the latched position to the released position. In another embodiment the arched bar 310 and/or the ligating portion 325 may be in the latched position in the body groove 412. The ligating clasp 300 may also be latched against a back of the linking body 400. For example, the body connection 450 may latch the ligating clasp 300. In an alternate embodiment, a device selected from the group consisting of a clasp, a latch, and a ligature wire latch the arched bar 310.

The ligating clasp 300 may hold the archwire 200 loosely within the slot 415. Alternatively, the ligating clasp 300 may hold the archwire 200 tightly within the slot 415 such that the archwire 200 does not move relative to the linking body 400. The latching force of the clasp 300 may be increased by closing and opening the handle 320 with pliers and/or other tools.

In one embodiment, the arched bar 310 only contacts the archwire 200 at two points or small two lines, reducing contact between the ligating clasp 300 and the archwire 200. Reducing contact reduces the friction between bracket 10 and archwire 200, allowing more freedom of movement of the archwire 200 relative to the linking body 400 along the archwire longitudinal axis 210.

FIG. 19 is a perspective-view drawing illustrating one embodiment of the connector 500. The connector 500 is the connector of FIGS. 9 and 10. The description of the connector 500 refers to elements of FIGS. 1-18, like numbers referring to like elements. The connector 500 includes the connector tail 515, an axial member 510, and the connector head 505. The connector 500 may be made of an elastic, high-resilience metal.

The connector tail 515 is depicted with a rectangular shape. However, the connector tail 515 may be formed in any shape. The connector tail 515 may be formed with a larger area perpendicular to the connector central axis 520 than an area of the axial member 510 perpendicular to the connector central axis 520. In one embodiment, the connector tail 515 is formed with an anti-aliasing shape, wherein the connector tail 515 will only conform to the base tooth face recess 165 in a single orientation.

The connector head 505 is depicted with a rectangular shape. However, the connector head 505 may be formed in any shape. The connector head 505 may be formed with a larger area perpendicular to the connector central axis 520 than the area of the axial member 510 perpendicular to the connector central axis 520. In one embodiment, the connector head 505 is formed with an anti-aliasing shape, wherein the connector head 505 will only conform to the body recess 440 in only a single orientation.

The connector 500 may be formed of an elastic material. The elastic material may be selected from the group consisting of rubber, a rubber metal alloy, and a flexible plastic. Alternatively, the connector 500 may be formed of an elastic, high-resilience metal. The elastic, high-resilience metal may be selected from the group consisting of a cobalt chromium nickel iron alloy, a nickel titanium alloy, a nickel titanium cobalt alloy, and a titanium nickel chromium copper alloy. Alternatively, the connector 500 may be formed of an elastic material.

The connector tail 515 may be inserted from the base connection 150 side of the base 100 through the base hole 170. The connector tail 515 may then be: hammered; pressed; preheated, hammered and pressed; welded; or the like to fit within the base recess 165 so that the connector tail 515 cannot be withdrawn through the base hole 170 to the base connection 150 side of the base 100.

Similarly, the connector head 505 may be inserted from the body connection 450 side of the linking body 400 through the body hole 470. The connection head 505 may then be: hammered; pressed; preheated, hammered and pressed; welded; or the like to fit within the body recess 440 so that the connector head 505 cannot be withdrawn through the body hole 470 to the body connection 450 side of the linking body 400. The connector tail 515 may deform to allow the connector tail 515 to pass through the base hole 170. The connector head 505 may also deform to allow the connector head 505 to pass through the body hole 470. In an alternate embodiment, the connector 500 is made without the head 505 and/or without the tail 515. The connector 500 may be welded to the base 100 and/or to the linking body 400.

In one embodiment, the axial member 510 is inserted through the base hole 170. The axial member 510 may pressed with a heated tool to form the connector tail 515. In addition, the axial member 510 may be inserted through the body hole 470 and pressed with the heated tool to form the connector head 505.

In one embodiment, the connector 500 comprises an axial member 510 formed of a rectangular closed spring coil. The connector head 505 may be welded and/or bonded to the linking body 400. Alternatively, the connector head 505 may be inserted through the body hole 470 and welded and/or bonded to the body recess 440. In addition, the connector tail 515 may be welded and/or bonded to the base 100. Alternatively, the connector tail 515 may be inserted through the base hole 170 and welded and/or bonded to the base recess 165.

In one embodiment, the connector head 505 and connector tail 515 are each formed with the same shape. The axial member 510 may initially have a plurality of connector heads 505/connector tails 515 for a plurality of connectors 500. A first connector head 505/connector tail 515 may be deformed to pass through the body hole 470 and the base hole 170. The first connector head 505/connector tail 515 then becomes the connector tail 515 of a first connector 500a. The first connector 500a is then cut from the axial member 510 after a second connector head 505/connector tail 515. The second connector head 505/connector tail 515 becomes the connector tail 515.

In a certain embodiment, the connector tail 515 is welded to the base 100. Alternatively, the connector tail 515 may be bonded to the base 100. The connector head 505 may be welded to the linking body 400. Alternatively, the connector head 505 may be bonded to the linking body 400.

In one embodiment, the dimensions of the axial member 510 are selected to generate different tensions when the connector 500 is stretched in different directions. For example, the connector 500 may generate a first tension when stretched more toward a connector horizontal axis 560 and generate a second tension when stretched more toward a connector vertical axis 555. In addition, the connector 500 may generate a third tension when stretched more along the connector central axis 520 and generate a fourth tension when twisted more around the connector central axis 520.

Figure 20:
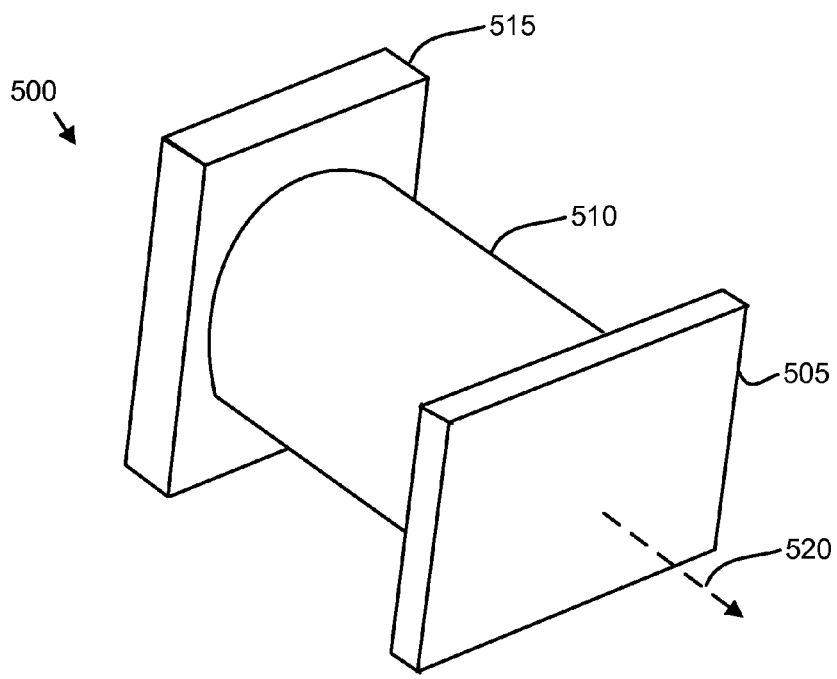
FIG. 20 is a perspective-view drawing illustrating one embodiment of a connector.

FIG. 20 is a perspective-view drawing illustrating one alternate embodiment of the connector 500. The connector 500 is the connector of FIG. 19. The description of the connector 500 refers to elements of FIGS. 1-19 like numbers referring to like elements. The connector 500 is shown with a cylindrically shaped axial member 510.

Figure 21:
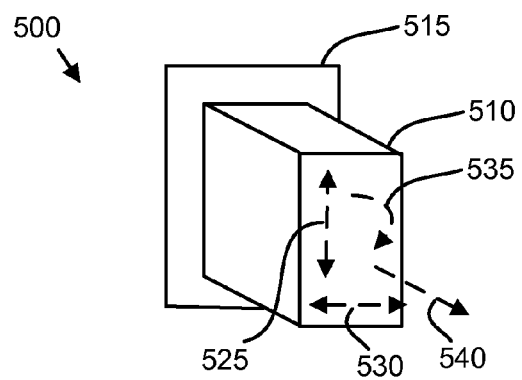
FIG. 21 is a cross-sectioned perspective view drawing illustrating the connector and forces and moments on the connector.

FIG. 21 is a cross-sectioned perspective view drawing illustrating the connector 500 and forces and moments on the connector 500. The connector 500 of FIG. 19 is shown cross sectioned through the axial member 510. A vertical force moment 525, a horizontal force moment 530, a twisting moment 535, and a stretching force moment 540 are shown.

In one embodiment, the connector 500 applies a tension between the linking body 400 and the base 100 until, motivating the linking body 400 and the base 100 toward a normal position. The specified force/moment may be different for different forces/moments of orthodontic movements and for different tooth types. Table 2 summarizes one embodiment of maximum moments that the connector 500 may apply to the tooth 5, including a vertical force moment 525, a horizontal force moment 530, a twisting moment 535, and a stretching force moment 540 for front teeth and back teeth. The moments are expressed in gram millimeters (gm mm) with an acceleration of one gravity. In one embodiment, the tension of the connector 500 must be increased for increased static friction between the base 100 and the linking body 400 and/or for other parameter changes. Alternatively, the tension of the connector 500 may be decreased.

TABLE 2

| Connector Tension | Front Teeth | Back Teeth |
| --- | --- | --- |
| Vertical 525 | 750 gm mm | 1500 gm mm |
| Horizontal 530 | 140 gm mm | 240 gm mm |
| Twist 535 | 1050 gm mm | 1800 gm mm |
| Stretching 540 | 1050 gm mm | 1800 gm mm |

In one embodiment, the dimensions of the axial member 510 are selected to generate tensions proportional to the maximum moments of Table 2. For example, the tension generated by stretching the connector 500 along the connector horizontal axis 530 for a front tooth 5 may be proportional to 140 gm mm while the tension generated by stretching the connector 500 along the connector vertical axis 525 for a front tooth may be proportional to 750 gm mm. Thus the tension generated by stretching the connector 500 in along the connector horizontal axis 530 may be 140/750 the tension generated by stretching the connector 500 along the connector vertical axis 525.

Figure 22:
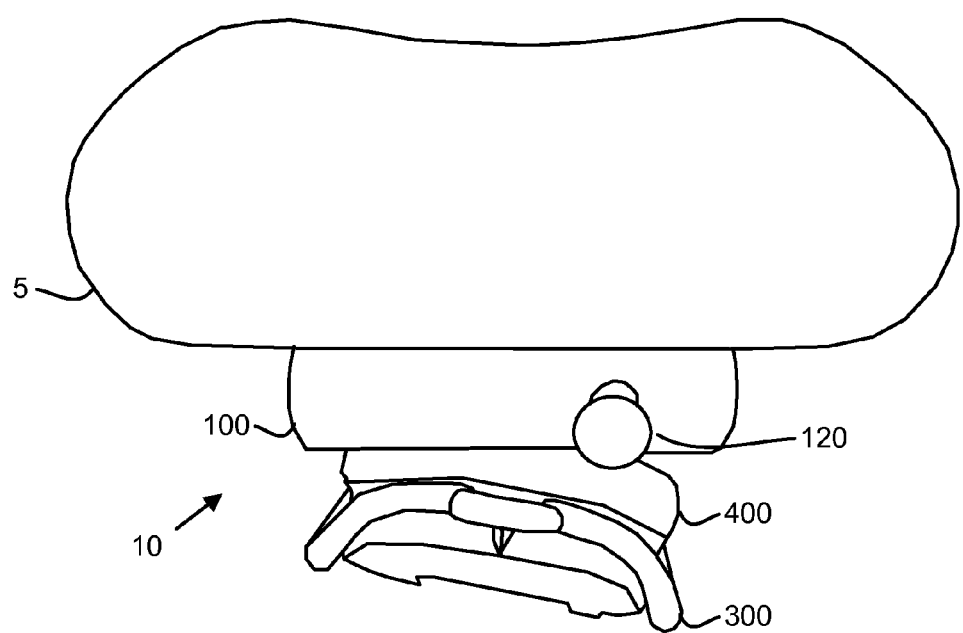
FIG. 22 is a top-view drawing illustrating one embodiment of a self-adjustable self-ligating orthodontic bracket mounted on a tooth.

FIG. 22 is a top-view drawing illustrating one embodiment of the bracket 10 of FIGS. 9 and 10. The description of the bracket 10 refers to elements of FIGS. 1-20, like numbers referring to like elements. The linking body 400 is repositioned in physical communication with the base 100 to an initial position. The connector 500 may apply a tension to the linking body 400 and the base 100 motivating the linking body 400 and the base 100 toward the normal position.

Figure 23:
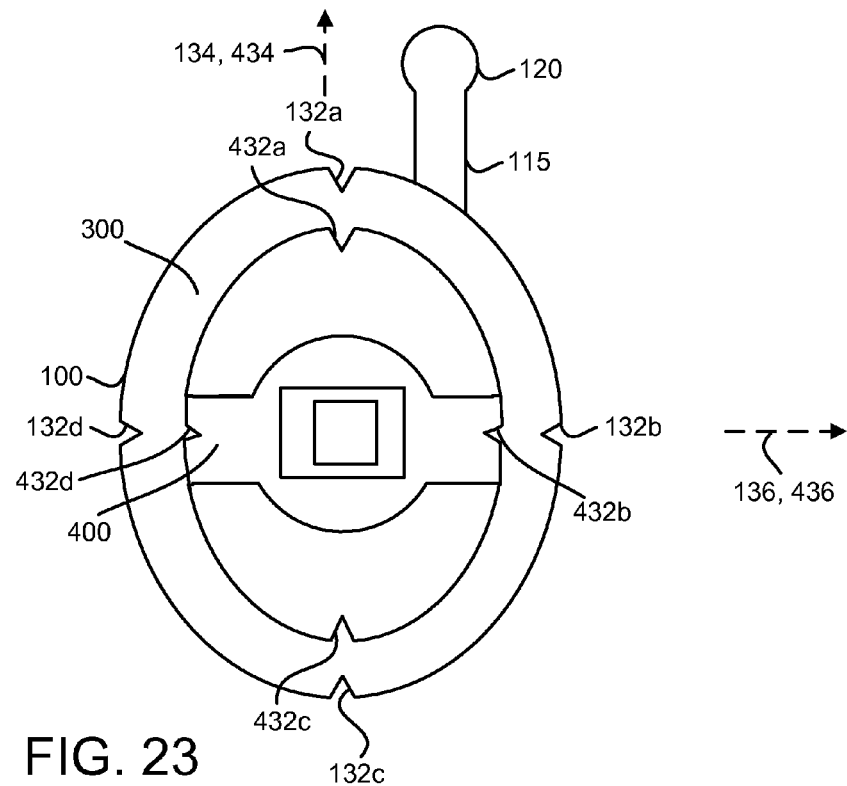
FIG. 23 is a front-view drawing illustrating one embodiment of indicator notches ones a linking body 400 and base.

FIG. 23 is a front-view drawing illustrating indicator notches 132, 432 on the linking body 400 and the base 100. The linking body 400 is the linking body 400 of FIGS. 9 and 10. The base 100 is the base 100 of FIGS. 9 and 10. The description of indicator notches 132, 432 refers to elements of FIGS. 1-22, like numbers referring to like elements. The indicator notches 132, 432 may be formed as slots, cuts, depressions, or the like.

In one embodiment, base indicator notches 132 may be molded with the base 100. Alternatively, the base indicator notches 132 may be machined into the base 100. The base indicator notches 132 may provide horizontal and vertical axis references to the orthodontist in aligning the base 100 on the tooth 5. In one embodiment, vertical base indicator notches 132a, 132c are aligned along a base vertical axis 134 of the base 100. In addition, horizontal base indicator notches 132b, 132d may be aligned along a base horizontal axis 136 of the base 100. In one embodiment, the vertical base indicator notches 132a,c and/or horizontal base indicator notches 132b,d can be aligned with respect to the vertical and/or horizontal planes of the tooth 5.

In one embodiment, body indicator notches 432 may be molded with the linking body 400. Alternatively, the body indicator notches 432 may be machined into the linking body 400. The body indicator notches 432 may provide horizontal and vertical axis references to the orthodontist in aligning the linking body 400 with the base 100. In one embodiment, vertical body indicator notches 432a, 432c are aligned along a body vertical axis 434 of the linking body 400. In addition, body horizontal indicator notches 432b, 432d may be aligned along a body horizontal axis 436 of the linking body 400. Alternatively, the vertical body indicator notches 432a,c and/or horizontal body indicator notches 432b,d can be aligned with respect to the vertical and/or horizontal planes of the tooth 5.

Figure 24:
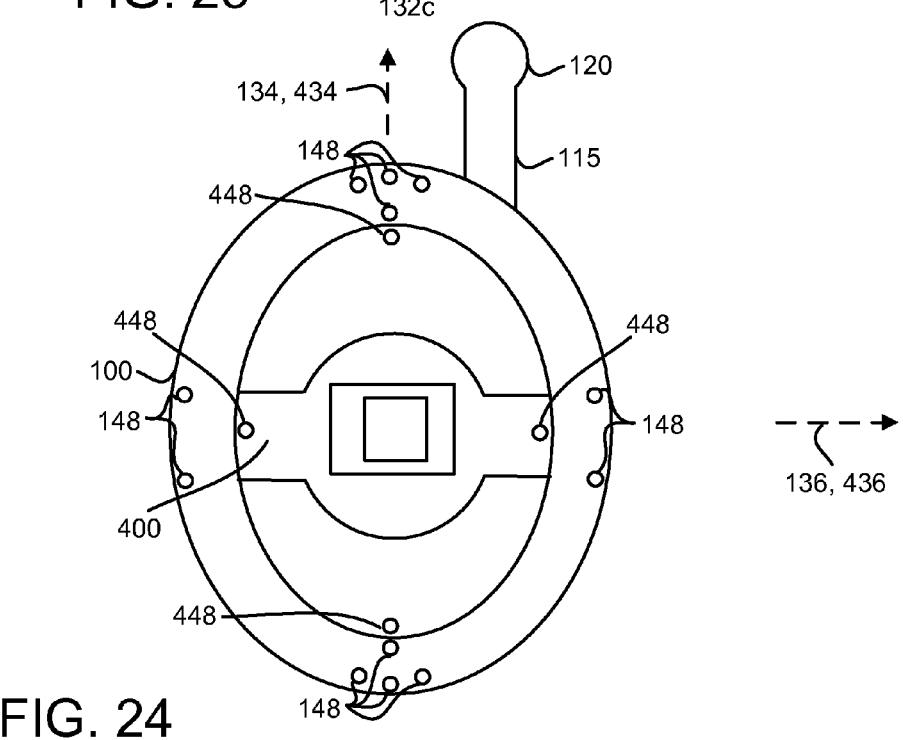
FIG. 24 is a front-view drawing illustrating one embodiment of indicator marks on a linking body and a base.

FIG. 24 is a front-view drawing illustrating indicator marks 148, 448 on the linking body 400 and the base 100. The linking body 400 is the linking body 400 of FIGS. 1 and 2. The base 100 is the base 100 of FIGS. 1 and 2. The description of indicator marks 148, 448 refers to elements of FIGS. 1-14, like numbers referring to like elements. The indicator marks 148, 448 may be formed as depressions, bumps, textured areas, or the like. In one embodiment, the indicator marks 148, 448 are colored.

The orthodontist may use the indicator marks 148, 448 to align the base 100 on the tooth 5 and the linking body 400 on the base 100. In one embodiment base indicator marks 148 and body indicator marks 448 may be used in combination with base indicator notches 132 and body indicator notches 432. The body indicator marks 448 and the base indicator marks 148 may be used to show the changed positions of the linking body 400 relative to the base 100.

Figure 25:
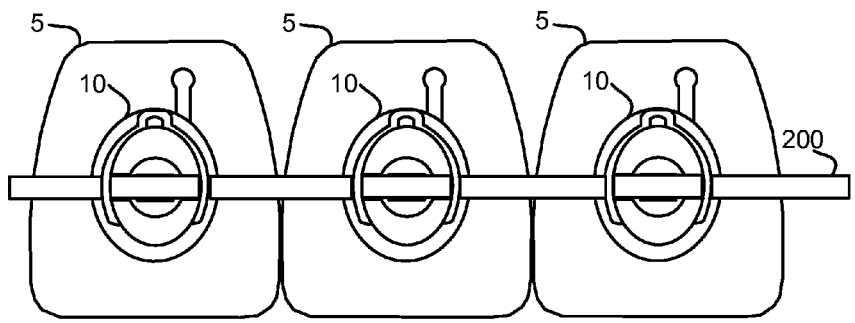
FIG. 25 is a front-view drawing illustrating one embodiment of brackets with an archwire.

FIG. 25 is a front-view drawing illustrating one embodiment of brackets 10 with the archwire 200. The brackets 10 are a plurality of brackets 10 of FIGS. 9 and 10. The description of the brackets refers to elements of FIGS. 1-24, like numbers referring to like elements. Although for simplicity three teeth 5 and three brackets 10 are shown, any number of brackets 10 may be employed on any number of teeth 5.

The archwire 200 passes through the slot 415 of each linking body 400 of each bracket 100 perpendicular to the base central axis 105 of each bracket 10. In addition, the archwire 200 forms a single vector without bends. As a result, the body central axis 405 may be co-axial with the base central axis 105 and the connector central axis 320 for each bracket 10.

In one embodiment, the archwire 200 may slide in the direction of the archwire longitudinal axis 210 through the slot 415. The sliding may be advantageous, allowing the archwire 200 to continue to apply a force to the tooth 5 as the tooth 5 is repositioned. Thus reducing the friction between the archwire 200 and the linking body 400 may improve the orthodontic function of the archwire 200 and bracket 10.

Figure 26:
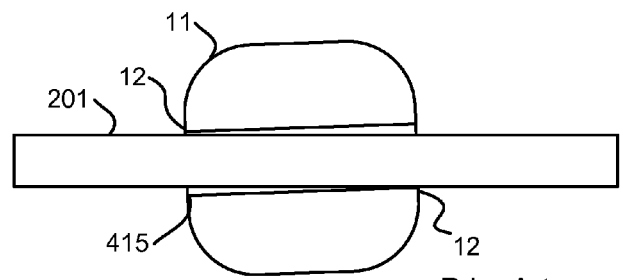
FIG. 26 is a front view drawing illustrating one embodiment of an archwire and simplified bracket of the prior art.

FIG. 26 is a front view drawing of an archwire 201 and simplified bracket 11 of the prior art. The archwire 201 is not aligned with a slot 415 of the bracket 11. The archwire 201 may not be aligned with the slot 415 because the bracket 11 was originally positioned at an angle to the archwire 201, because a tooth and the bracket 11 bonded to the tooth moved, because of a changing of the position of the bracket 11 relative to the archwire 201, and/or because the archwire 201 was repositioned. As a result, the archwire 201 is shown contacting the bracket 11 at contact points 12. This contact increases the friction between the archwire 201 and the bracket 11, reducing the ability of the archwire 201 to slide relative to the bracket 11.

In the past, when an archwire 201 was unable to slide easily relative to a bracket 11 because of high friction between the bracket 11 and the archwire 201 as a result of the slot 415 not being parallel to the archwire 201, the orthodontist was required to manually adjust the archwire 201 with loops and/or bends. Alternatively, the orthodontist may have used more wires, used wires with different flexibilities, and/or used brackets 11 more parallel with the archwire 201. These adjustments could be required at the start of the orthodontic treatment and/or later in the orthodontic treatment and were often time consuming.

However, the embodiments of the bracket 10 described herein self-adjust so that the axis of the slot 415 is more parallel with the archwire 200 passing in the slot 415. This automatically reduces the friction between the archwire 200 and the linking body 400 throughout the treatment. As a result, the embodiments of the bracket 10 described herein support the combining of more than one movement both concurrently and in different planes. For example the brackets 10 can make leveling and aligning movements in the vertical plane concurrently with sliding movements in the horizontal plane.

Figure 27:
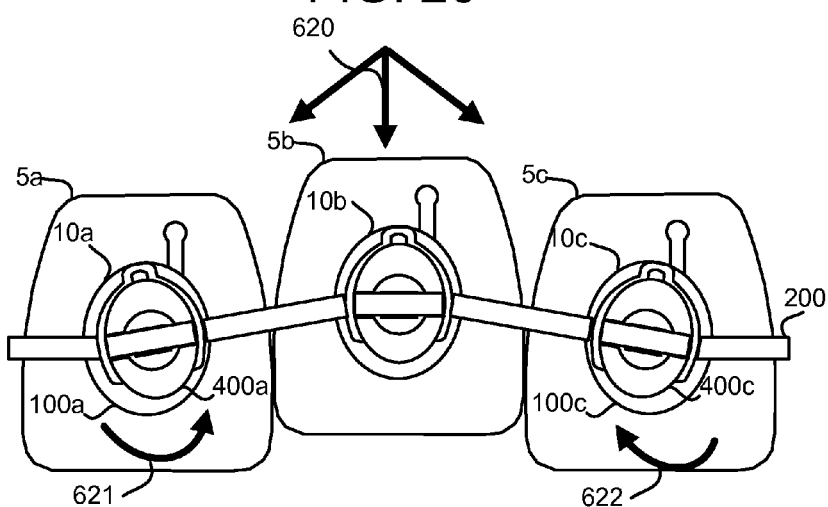
FIG. 27 is a front-view drawing illustrating one embodiment of brackets with repositioned linking bodies.

FIG. 27 is a front-view drawing illustrating one embodiment of brackets 10 with repositioned linking bodies 400. The brackets 10 are a plurality of brackets 10 of FIGS. 9 and 10. The description of the brackets refers to elements of FIGS. 1-25, like numbers referring to like elements.

The archwire 200 is depicted as bent to apply a downward force 620 on a second bracket 10b. In response to the bending of the archwire 200, a first linking body 400a of a first bracket 10a is positioned from the normal position to an initial position by rotating counter-clockwise about the body central axis 405 of the first linking body 400a, and a third linking body 400c of a third bracket 10c is positioned from the normal position to an initial position by rotating clockwise about the body central axis 405 of the third linking body 400c. In addition, the second linking body 400b of the second bracket 10b may be repositioned by tilting downward about the body central axis 405 in the same direction of the force 620.

As a result, the friction between the archwire 200 and each linking body 400 is reduced since the bended archwire 200 became more parallel with the bracket slots 415, allowing the archwire 200 to slide in the slots 415 more easily along the archwire longitudinal axis 210. The reduced friction between the archwire 200 and the linking body 400 may lead to faster orthodontic movements. If the two brackets 10a and 10c have increased friction with the archwire 200, the first and third linking bodies 400a, 400c may tend to tilt towards the bracket 10b. This movement of the teeth 5 and bending in the archwire 200 is well known to those of skill in the art as second order movement or bending.

In one embodiment, the connector 500 applies a moment between the linking body 400 and the base 100 to motivate the linking body 400 toward the normal position with the base 100. For example, the linking body 400a of the first bracket 10a may adjust position in response to the angle of the archwire 200 by rotating counter-clockwise. In response, a first connector 500a of the first bracket 10a may apply a counter-clockwise moment 621 to the first base 100a. Similarly, the linking body 400c of the third bracket 10c may adjust position in response to the angle of the archwire 200 by rotating clockwise. In response, a third connector 500c of the third bracket 10c may apply a clockwise moment 622 to the third bracket base 100c.

As each linking body 400 self-adjusts to align with the archwire 200, the friction between the archwire 200 and the linking body 400 decreases, allowing a faster, less restricted movement the archwire 200. In addition, the connectors 500 motivate the linking bodies 400 and the bases 100 to self-adjust to the normal position, transmitting moments and forces from each body 400 to each base 100 that apply a steady force that motivates the tooth 5. As a result, the movement speed of tooth 5 is increased while maintaining tooth roots perpendicular with the archwire 200 throughout the treatment. As the linking bodies 400 adapt with the archwire 200, the linking bodies 400 increase the downward force 620 of the archwire 200 on the second bracket 10b.

Figure 28:
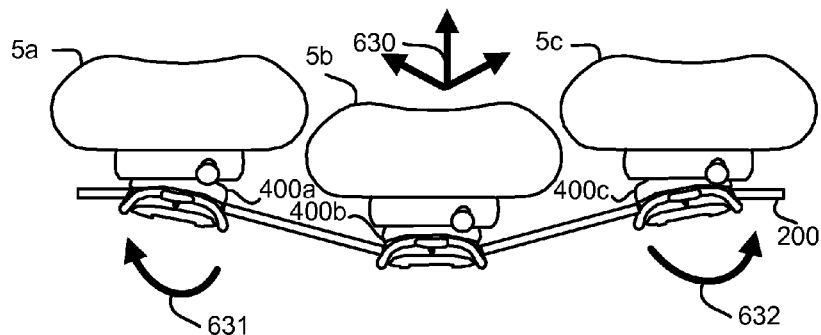
FIG. 28 is a top-view drawing illustrating one embodiment of brackets with repositioned linking bodies.

FIG. 28 is a top-view drawing illustrating one alternate embodiment of brackets 10 with repositioned linking bodies 400. The brackets 10 are a plurality of brackets 10 of FIGS. 9 and 10. The description of the brackets refers to elements of FIGS. 1-27, like numbers referring to like elements.

The archwire 200 is depicted as bent outward to apply a backward force 630 on the second bracket 10b. This movement of the teeth 5 and bending in the archwire 200 is well known to those of skill in the art as first order movement or bending.

The first linking body 400a is positioned to an initial position by rotating the first linking body 400a clockwise about the body vertical axis 434 (shown in FIG. 23) of the first linking body 400a in response to a clockwise moment 631 applied by the archwire 200 on the first linking body 400a so that the body central axis 405 of the first linking body 400a is at an angle to the base central axis 105 of the first base 100a. As a result, the first bracket 10a linking body 400a is repositioned to be more parallel with the archwire 200 and the friction between the first bracket 10a and archwire 200 is minimized making the orthodontic movement easier and faster.

Because the first linking body 400a adjusts to the bended archwire 200 passing through the first linking body 400a, the first linking body 400a takes the high tension from the archwire 200 and delivers the tension slowly with controlled intensity from the first connector 500a to the first bracket base 100a to the first tooth 5a. As a result, the orthodontic movement is accomplished while causing less pain to the tooth 5a and the periodontal ligament. In addition, the orthodontic movement is faster and easier because the archwire 200 provides a low, continuous force ideal for best tooth movements.

The third linking body 400c is positioned to an initial position by rotating the third linking body 400c counter-clockwise about a body vertical axis 434 of the third linking body 400c in response to a counter-clockwise moment 632 applied by the archwire 200 on the third linking body 400c so that the body central axis 405 of the third linking body 400c is at an angle to the base central axis 105 of the third base 100c.

In addition, the friction between the archwire 200 and each linking body 400 is reduced by the rotation of the linking bodies 400, allowing the archwire 200 to slide more easily along the archwire longitudinal axis 210. As a result, the linking body 400c of the third bracket 10c is repositioned to be more parallel with the archwire 200 and the friction between the third bracket 10c and archwire 200 is minimized making the orthodontic movement easier and faster.

Because the third linking body 400c adjusts to the bended archwire 200 passing through the third linking body 400c, the third linking body 400c takes the high tension from the archwire 200 and delivers the tension slowly with controlled intensity from the third connector 500c to the third bracket base 100c to the third tooth 5c. As a result, the orthodontic movement is accomplished with less pain on the tooth and periodontal ligament. In addition, the orthodontic movement is faster and easier because the archwire 200 provides a low, continuous force ideal for best tooth movements.

Figure 29:
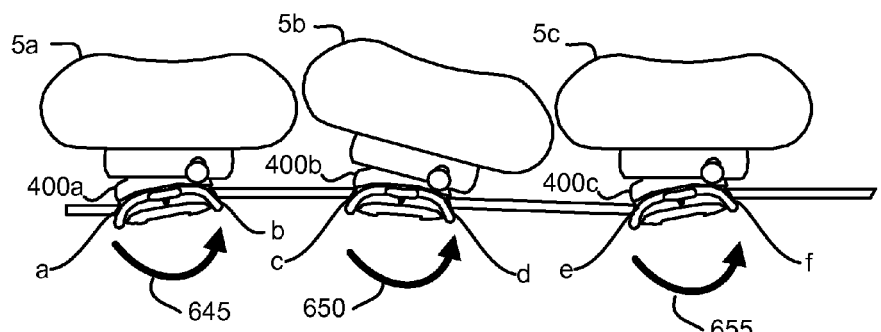
FIG. 29 is a top-view drawing illustrating one alternate embodiment of brackets with repositioned linking bodies.

FIG. 29 is a top view drawing illustrating an alternate embodiment of brackets 10 with repositioned linking bodies 400. The brackets 10 are a plurality of brackets 10 of FIGS. 9 and 10. The description of the brackets refers to elements of FIGS. 1-28, like numbers referring to like elements.

The second tooth 5b is initially rotated clockwise on the second tooth's vertical axis 15. The archwire 200 is depicted as bent to apply a counter-clockwise moment 650 to the second bracket 10b linking body 400b. The moment 650 causes an immediate counter-clockwise movement of the second linking body 400b about the body vertical axis 434, stretching the connector 500b of the second bracket 10b. This counter-clockwise movement will make the edge c of second linking body 400b more forward and the edge d more backward, making the slot 415 of the second linking body 400b more parallel with the archwire 200. As a result, the moment of the archwire 200 will be transmitted slowly with controlled intensity through the second connector 500b to the second base 100b to the second tooth 5b, so that the orthodontic movement is more consistent, faster and with less pain.

The movement of the second tooth 5b is well known to those of skill in the art as rotation movement. The self adjustment of the linking body 400b with the archwire 200 passing in the second linking body 400b keeps the slot 415 of second bracket 10b more parallel with the archwire 200, reducing the friction between the slot 415 and archwire 200 and increasing the speed and efficiency of the orthodontic movement.

In response to the bending of the archwire 200, the second linking body 400b self-adjusts by rotating counter-clockwise about the vertical axis 434 of the second linking body 400b. The self-adjustment of the second linking body 400b applies a backward tension from the archwire 200 on the right side of the first linking body 400a. The first linking body 400a then is positioned to an initial position by rotating the first linking body 400a counter-clockwise about the vertical axis 434 of the first linking body 400a in response to the archwire 200 applying a counter-clockwise moment 645 on the first linking body 400a so that the edge b of the first linking body is motivated forward.

In response to the bending of the archwire 200, the second linking body 400b self-adjusts by rotating counter-clockwise about the vertical axis 434 of the second linking body 400b, applying a forward tension from the archwire 200 on the left side of the third linking body 400c. The third linking body 400c is positioned to an initial position by rotating the third linking body 400c counter-clockwise about the vertical axis 434 of the third linking body 400c in response to a counter-clockwise moment 655 applied by the archwire 200 so that the edge e of the third linking body is motivated forward. In addition, the friction between the archwire 200 and each linking body 400 is reduced since all linking bodies 400 self adjust by aligning to be more parallel with the archwire 200, allowing the archwire 200 to slide more easily along the archwire longitudinal axis 210.

By self-adjusting the linking body's position in response to the position of the archwire 200, the moment, moment angle, force, and force angle applied by the archwire 200 to a tooth 5 are adjusted automatically. The linking body 400 adjusts to make the slot 415 of the linking body 400 more parallel with the curved archwire 200 passing through the slot 415, decreasing the need to bend the archwire 200 to pass in all brackets 10. As a result, the archwire 200 positioned more rapidly while decreasing the friction and increasing the speed and quality of the movement of the tooth 5. As a result, the orthodontist may apply the brackets 10 more rapidly and with greater therapeutic effect. In addition, the overall treatment time can be shorter and with less pain since the tension from the archwires 200 is received by the brackets 10 and transmitted gently to the teeth 5.

Figure 30:
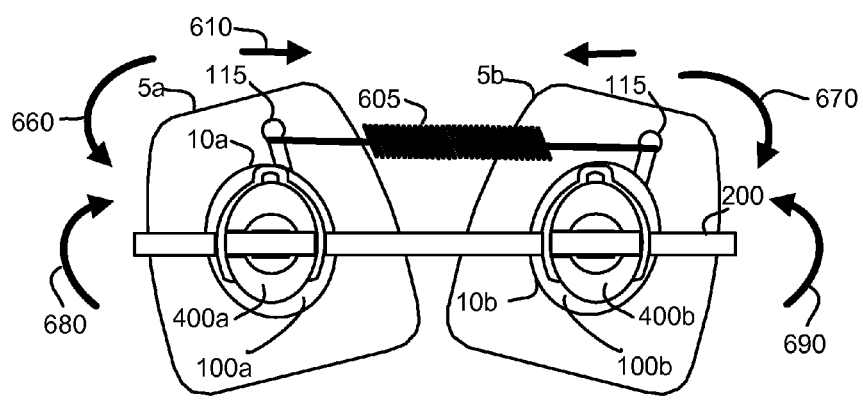
FIG. 30 is a front-view drawing illustrating one alternate embodiment of brackets with repositioned linking bodies.

FIG. 30 is a front-view drawing illustrating one embodiment of applying a sliding force to brackets 10. The brackets 10 are the brackets of FIGS. 9 and 10. The description of the brackets 10 refers to elements of FIGS. 1-29, like numbers referring to like elements. The movement of the brackets 10 along the archwire 200 to close or open a space between teeth 5 to the right or left of a tooth 5 in the horizontal plan may be called sliding movement by those of skill in the art. A closed coil spring 605 is depicted as applying a sliding force 610 to the teeth 5. The closed coil spring can be replaced with an elastic power chain, pulling device, or the like.

Figure 33:
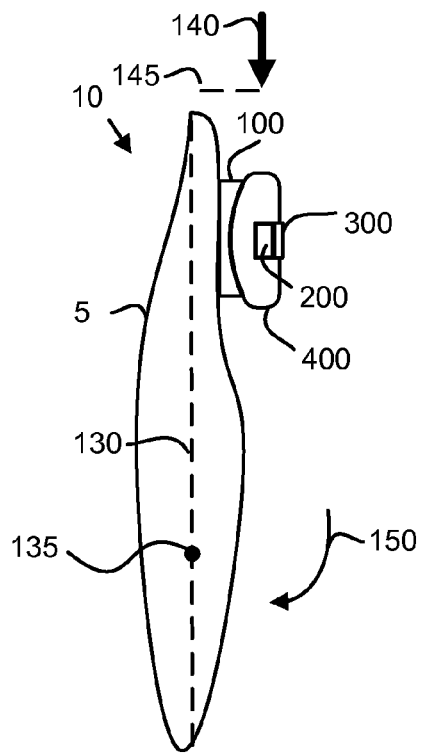
FIG. 33 is a side view drawing illustrating one embodiment of a bracket and archwire moving a tooth.

The closed coil spring 605 is connected to the hooks 120 of the first and second brackets 10a, b. The closed coil spring 605 applies the sliding force 610 that moves the teeth 5 closer together. When applying this force to move the teeth 5 closer together, the crowns of the teeth 5 are motivated closer together faster than the roots of the teeth 5 since the center of resistance of each tooth 5 is close to the apical third of the tooth root as shown in FIG. 33. As a result, during the start of the movement the closed coil spring 605 may apply a counter-clockwise moment 660 to the first tooth 5a and a clockwise moment 670 to the second tooth 5b. However, when the teeth 5 come in contact at the crowns, the closed coil spring 605 may apply a clockwise moment 680 to the first tooth 5a and a counter-clockwise moment 690 to the second tooth 5b, rotating and straightening the teeth 5.

In addition, the first linking body 400a rotates clockwise on the first base 100a to an initial position of the first linking body 400a and the first base 100a. The connector 500 of the first bracket 10a applies a moment between the first linking body 400a and the first base 100a motivating the first linking body 400a toward the normal position and increasing the clockwise moment 680 on the first tooth 5a. The second linking body 400b rotates counter-clockwise on the second base 100b to an initial position of the second linking body 400b and the second base 100b. The connector 500 of the second bracket 10b applies a moment between the second linking body 400b and the second base 100b motivating the second linking body 400b toward the normal position and increasing the counter-clockwise moment 690 on the second tooth 5b.

Applying the sliding force 610 at the handle 115 and the self adjusting of the linking bodies 400 due to the flexibility of the connectors 500 allows the slot 415 of each bracket 10 to be in a position that is more parallel with the archwire 200. As a result there will be less friction between the slot 415 and the archwire 200 and faster and easier movement until the teeth 5 contact at the crowns.

In one embodiment, the application of the sliding force 610 reduces the need to bend the archwire 200 to apply the desired moments. This described sliding force movement can be used for teeth 5 in different initial angulations in the dental arch. The linking body 400 for each tooth adapts to be more parallel with the archwire 200 passing in the slot 415 and the flexibility of the connector 500 repositions the teeth 5 in the desired position. For example, the teeth 5 may be more parallel to each other with the roots more perpendicular with the archwire 200.

Figure 31:
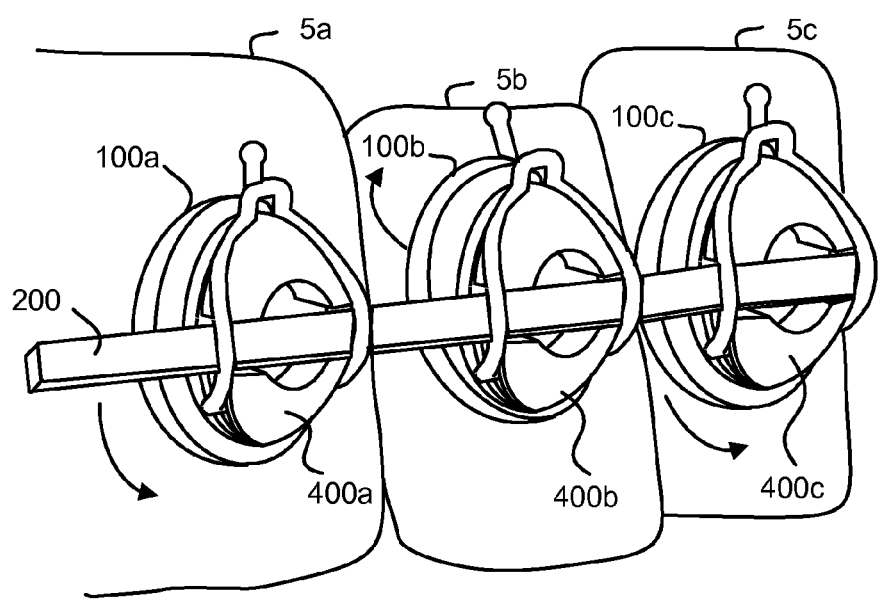
FIG. 31 is a perspective-view drawing illustrating one embodiment of brackets with repositioned linking bodies.

FIG. 31 is a perspective-view drawing illustrating one embodiment of brackets 10 with repositioned linking bodies 400. The brackets 10 are a plurality of brackets 10 of FIGS. 1 and 2. The description of the brackets refers to elements of FIGS. 1-30, like numbers referring to like elements.

The second tooth 5b is rotated backward from the archwire 200, with the archwire 200 is depicted as twisted to apply a moment on a second bracket 10b making a tip of a root of a second tooth 5b move to the outside of the mouth and the tip of the crown of the second tooth 5b incline to the inside of the mouth. The movement of the teeth 5 and bending in the archwire 200 is well known to those of skill in the art as torque movement.

This movement typically may be achieved in one of two ways. First, by twisting the archwire 200 at the first tooth 5a and third tooth 5c when using a less flexible archwire 200 with less spring, such as a stainless steel archwire 200. Alternatively, by using a more flexible archwire 200 with more spring, such as a nickel titanium archwire 200. The more flexible archwire 200 may have a large cross section and fit tightly in the slot 415 of the linking body 400 so the archwire 200 will transmit the corrective moment to the second tooth 5b automatically. In the depicted example a twisting force is applied to the second tooth 5b in a movement known to those of skill in the art as a moment torque.

In response to the twisting moment of the archwire 200, a first linking body 400a of a first bracket 10a self-adjusts by rotating slightly down with the body central axis 405 of the first linking body 400a at an angle to the base central axis 105 of the first base 100a and a third linking body 400c of a third bracket 10c self-adjusts by rotating slightly down with the body central axis 405 of the third linking body 400c at an angle to the base central axis 105 of the third base 100c, while the second linking body 400b of a second bracket 10b self-adjusts by rotating up with the body central axis 405 of the second linking body 400b at an angle to the base central axis 105 of the second base 100b. This self adjustment keeps the linking body's slot 415 more parallel with the longitudinal axis 210 of the archwire 200, resulting in less friction, faster and easier movements. As a result, an orthodontist may combine more than one movement concurrently.

The slot 415 will self-adjust with the moment of the archwire 200 and then spring back and transfer the moment to the tooth 5 because of the flexibility of the connector 500. This torque movement is also important when the teeth are initially on the dental arch in different moment positions for different proclinations and inclinations so the slot 415 of each bracket 10 will adjust itself to make the inside surfaces of the slot 415 more parallel with the outside surfaces of the archwire 200 and then the moment will be transferred to the tooth 5 when the connector 500 goes back to the connector's original shape.

Figure 32:
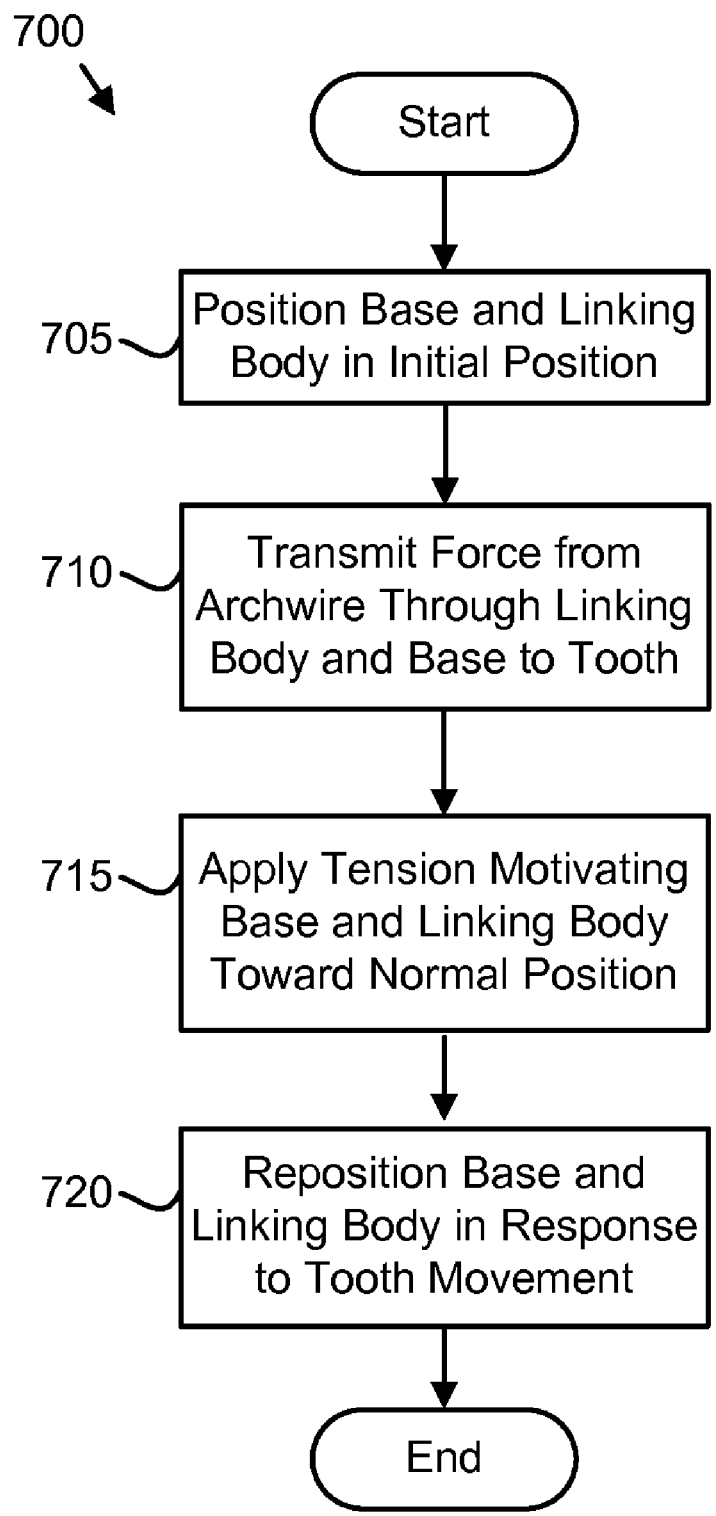
FIG. 32 is a flow chart diagram illustrating one embodiment of an orthodontic bracket positioning method.

FIG. 32 is a flow chart diagram illustrating one embodiment of an orthodontic bracket positioning method 700. The method 700 embodies the functions of the brackets 10 of FIGS. 1-31. The description of the method 700 refers to elements of FIGS. 1-31, like numbers referring to like elements.

The method 700 starts, and in one embodiment, the base 100 and the linking body 400 are positioned 705 in an initial position. The orthodontist may position the base 100 and the linking body 400 of the bracket in the initial position. The archwire 200 may be in a first archwire position and may transmit 710 a force through the linking body 400 and the base 100 to the tooth 5. The force may motivate the tooth 5 to reposition relative to a dental arch.

The connector 500 applies 715 a tension between the base 100 and the linking body 400. The tension motivates the linking body 400 and the base toward a normal position. In one embodiment, the tension repositions 720 the base 100 and the linking body 400 to a second position as the tooth 5 is repositioned in response to the force and the method 700 ends. The second position may be along an arc between the initial position and the normal position. In one embodiment, the force repositions the archwire 200 to a second archwire position as the tooth is repositioned relative to the dental arch.

FIG. 33 is a side view drawing illustrating one embodiment of a bracket 10 and archwire 200 moving a tooth 5. The bracket 10 is the bracket 10 of FIG. 4, but one of skill in the art will recognize that other embodiments of the bracket 10 may be employed. The description refers to elements of FIGS. 1-32, like numbers referring to like elements. The linking body 400 forms an initial position with the base 100.

The archwire 200 applies a force 140 to the bracket 10. The force 140 is applied at a moment arm 145 from a longitudinal axis 130 of the tooth 5. As a result, the force 140 results in a clockwise moment 150 about a center of resistance 135 for the tooth 5.

Figure 34:
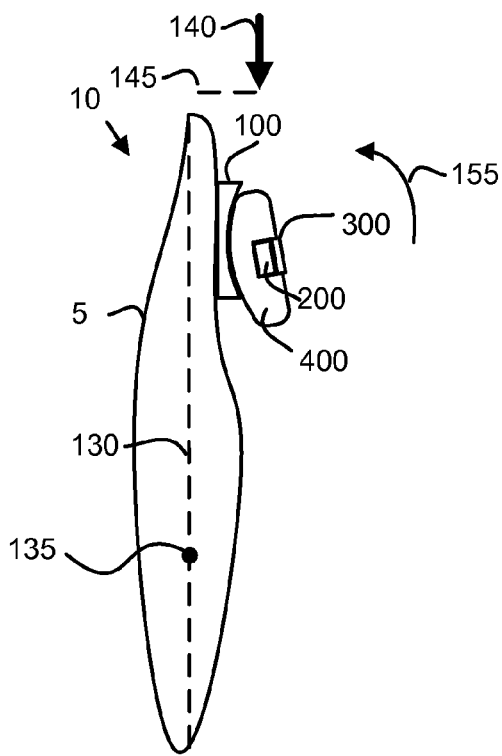
FIG. 34 is a side view drawing illustrating one embodiment of a bracket self-adjusting in response to a force.

FIG. 34 is a side view drawing illustrating one embodiment of a bracket 10 self-adjusting in response to a force 140. The bracket 10, tooth 5, and force 140 are the bracket 10, tooth 5, and force 140 of FIG. 33. The description refers to elements of FIGS. 1-34, like numbers referring to like elements.

The linking body 400 is shown self-adjusting in response to the force 140 by repositioning to a second position. As a result, the archwire 200 is twisted about the archwire longitudinal axis 210 so that the archwire 200 exerts a counter-clockwise moment 155 about the center of resistance 135, mitigating the clockwise moment 150 of the force 140.

This described moment adjustment function may be due to the base connection 150 convex shape, and body connection 450 concave shape. The base connection 150 and body connection 450 sliding relative to each other create an adjustment moment. The movements in FIGS. 33 and 34 are exemplary of movements. However, one of skill in the art will recognize that the adjustment moment of the linking body 400 and base 100 may be applied in all movements and directions since the forces applied on the bracket 10 cause the base connection 150 and body connection 450 to slide on each other in all directions.

The described embodiments allow brackets 10 to be easily secured to and positioned relative to the archwire 200. In addition, the linking body 400 self-adjusts relative to the base 100, simplifying fitting the bracket 10. Thus an orthodontic assistant may be able to position the brackets 10. In addition, the orthodontist may position and secure the brackets 10 more quickly, saving time and expense. For example, the self-adjustment of the linking body 400 and body 100 may reduce a number of archwires 200 used, and reduce the need to bend or otherwise position the archwires 200.

The linking body 400 may self-adjust in position and rotation relative to the base 100. By self-adjusting, the linking body 400 reduces stress on the tooth 5 from the archwire 200, increase the force vector that may be applied to the tooth 5. Thus self-adjusting of the linking body 400 may lesson pain, lessen root and bone socket injury, and lessen damage to the periodontal ligament.

The self-adjustment of the linking body 400 and base 100 allows increased elasticity of the archwire 200, increased moment applied to the tooth 5, and an increase in the dimensions of archwires 200 used early in treatment. In addition, the embodiments of the present invention may lessen a number of archwires 200 used in treatment, as well as lessening the overall time of treatment and time per each treatment visit.

The self-adjusting of the linking body 400 and base 100 also allows the archwire 200 to impart different forces and moments to each tooth 5, with reducing the bending and other adjustment of the archwire 200. An orthodontist may be able to use a single archwire 200 to apply a variety of forces and moments.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a base comprising a tooth face for bonding to a surface of a tooth;
   a linking body comprising a body connection physically interfacing with a base connection of the base and in physical communication with an archwire in a first archwire position in a slot of the linking body, the archwire transmitting a force to the linking body; and
   a stretchable connector applying a tension between the linking body and the base motivating the linking body and the base toward a normal position, repositioning the linking body relative to the base as the archwire is repositioned, wherein the tension of the stretchable connector self adjusts the bracket by the applied tension as the bracket motivates the tooth toward a second position.

2. The orthodontic bracket of claim 1, wherein the base and the linking body form an initial position.

3. The orthodontic bracket of claim 1, the tension repositioning the linking body and the base to the second position as the tooth is repositioned in response to the force.

4. The orthodontic bracket of claim 3, wherein the second position is along an arc between the initial position and the normal position.

5. The orthodontic bracket of claim 3, wherein the force repositions the archwire to a second archwire position as the tooth is repositioned.

6. The orthodontic bracket of claim 5, wherein the base connection is a concave face and the body connection is convex face.

7. The orthodontic bracket of claim 1, wherein the connector is a closed spring coil welded to the base and to the linking body.

8. The orthodontic bracket of claim 1, wherein the connector comprises a flexible axial member, a connector tail attached to the flexible axial member and fitting within a base recess of the base tooth face, the axial member passing through a base hole and a body hole, and the connector further comprising a connector head attached to the axial member, fitting within a body recess, and anchoring the connector to the body.

9. The orthodontic bracket of claim 8, wherein the flexible axial member comprises an elastomer.

10. The orthodontic bracket of claim 8, wherein the connector tail is formed with a first anti-aliasing shape and the base tooth face recess is formed to receive the first anti-aliasing shape.

11. The orthodontic bracket of claim 1, the base further comprising a base vertical indicator aligned along a base vertical axis of the base and a base horizontal indicator aligned along a base horizontal axis of the base and the linking body comprising a body vertical indicator aligned along a body vertical axis of the linking body and a body horizontal indicator aligned along a body horizontal axis of the linking body.

12. The orthodontic bracket of claim 11, wherein the base vertical indicator, the base horizontal indicator, the body vertical indicator, and the body horizontal indicator are selected from the group consisting of marks and grooves.

13. The orthodontic bracket of claim 1, the base comprising a base connection depression and the linking body comprising a body connection depression, wherein the connector is displaced from the base central axis within the base connection depression and the linking body depression.

14. The orthodontic bracket of claim 1, the linking body comprising a ligating clasp that removably secures the archwire to the linking body.

15. The orthodontic bracket of claim 14, the ligating clasp comprising an arched bar with a ligating portion and a first end and a second end rotating about a socket axis, the arched bar rotating about a socket axis to a latched position that secures the archwire to the linking body, wherein the ligating portion is latched to the linking body in the latched position, and the arched bar further rotating about the socket axis to a released position that allows the archwire to disengage from the body.

16. The orthodontic bracket of claim 15, the linking body comprising a slot between a first ridge and a second ridge and the arched bar securing the archwire in the latched position within the slot, the second ridge comprising a first socket and a second socket along the socket axis that receive the first end and the second end, the linking body further comprising a body groove encircling the linking body perpendicular to a central axis of the linking body.

17. The orthodontic bracket of claim 16, the body groove comprising a lip on the first ridge latching the ligating portion of the arched bar and preventing the arched bar from rotating from the latched position to the released position and another lip on the opposing ridge, the lip releasing the arched bar to rotate to the released position if the archwire force exceeds a ligating threshold.

18. The orthodontic bracket of claim 16, the body connection latching the ligating portion of the arched bar and preventing the arched bar from rotating from the latched position.

19. The orthodontic bracket of claim 16, the body groove receiving orthodontic accessories selected from the group consisting of O-shaped elastomeric bands, elastic power chains, and metal ligating wires.

20. The orthodontic bracket of claim 1, wherein the linking body is repositioned relative the base in a motion selected from away from the base, across the curve of the base, and all rotations relative to the base.

* * * * *